United States Patent
Toumazou et al.

(10) Patent No.: US 10,093,965 B2
(45) Date of Patent: Oct. 9, 2018

(54) METHOD AND APPARATUS FOR ANALYSING A BIOLOGICAL SAMPLE

(71) Applicant: DNANUDGE LIMITED, London (GB)

(72) Inventors: Christofer Toumazou, London (GB); Stuart Bhimsen Lowe, Melbourn (GB); Steven William Green, Melbourn (GB); Piers Sebastian Harding, Melbourn (GB); Giles Hugo William Sanders, Melbourn (GB); Nicholas James Wooder, Melbourn (GB); Andreas Augustinus Werdich, St. Albans (GB); Michiel Clemens Rene Twisk, Cambridge (GB); Rene Heinz Joaquim Zander, Melbourn (GB); Jonathan Casey, Cambridge (GB); Hannah Victoria Hare, Melbourn (GB); Richard Lintern, Cambridge (GB); Stephanie Weichert, Melbourn (GB); Steven James Wakefield, Baldock (GB); Kathrin Herbst, Cambridge (GB); Luciano Zanchet, Melbourn (GB)

(73) Assignee: DNA NUDGE LIMITED, London (GB)

( * ) Notice: Subject to any disclaimer, the term of this patent is extended or adjusted under 35 U.S.C. 154(b) by 0 days.

(21) Appl. No.: 15/714,160

(22) Filed: Sep. 25, 2017

(65) Prior Publication Data
US 2018/0087097 A1   Mar. 29, 2018

(30) Foreign Application Priority Data
Sep. 23, 2016   (GB) .................................. 1616174.7

(51) Int. Cl.
*C12Q 1/6827*   (2018.01)
*B01L 3/00*   (2006.01)
(Continued)

(52) U.S. Cl.
CPC ............ *C12Q 1/6827* (2013.01); *B01L 3/502* (2013.01); *B01L 3/50273* (2013.01);
(Continued)

(58) Field of Classification Search
CPC ............ B01L 2400/0644; B01L 3/502; B01L 2200/0621; B01L 2200/10; G06F 19/321;
(Continued)

(56) References Cited

U.S. PATENT DOCUMENTS

| 5,284,753 A | 2/1994 | Goodwin |
| 5,935,858 A | 8/1999 | Herst |

(Continued)

FOREIGN PATENT DOCUMENTS

| KR | WO2016/117726 | * | 7/2016 | ................ B01L 7/00 |
| WO | 2014/008381 A2 | | 1/2014 | |

(Continued)

OTHER PUBLICATIONS

Spurgeon et al. (PLoS ONE Feb. 2008, vol. 3, Issue 2, e1662) (Year: 2008).*

(Continued)

*Primary Examiner* — Sally A Merkling
(74) *Attorney, Agent, or Firm* — Saul Ewing Arnstein & Lehr LLP

(57) ABSTRACT

A system for preparing and analyzing a sample of biological material, including a test cartridge having a first housing defining a flow-through chamber, a second housing defining a central space within which the first housing is at least partially located. The first housing is rotatable relative to the second housing, and the second housing defines a plurality (Continued)

of circumferentially spaced chambers, one of the chambers having an inlet for receiving a sample, at least one of the chambers containing a liquid reagent, and at least one of the chambers comprising an analysis module, the chambers of the second housing each having an opening into the central space. The first housing has one or more openings into the central space so that openings can be selectively aligned with one of the openings into the chambers of the second housing by relative rotation of the first housing and second housings.

20 Claims, 28 Drawing Sheets

(51) Int. Cl.
*B01L 7/00* (2006.01)
*C12Q 1/6825* (2018.01)
*G01N 27/414* (2006.01)
*G06F 19/00* (2018.01)
*G06Q 30/00* (2012.01)

(52) U.S. Cl.
CPC .......... *B01L 7/5255* (2013.01); *C12Q 1/6825* (2013.01); *G01N 27/4145* (2013.01); *G06F 19/00* (2013.01); *G06F 19/30* (2013.01); *G06Q 30/00* (2013.01); *B01L 2200/0642* (2013.01); *B01L 2200/0684* (2013.01); *B01L 2200/10* (2013.01); *B01L 2300/025* (2013.01); *B01L 2300/047* (2013.01); *B01L 2300/0636* (2013.01); *B01L 2300/0654* (2013.01); *B01L 2300/0803* (2013.01); *B01L 2300/0848* (2013.01); *B01L 2300/0864* (2013.01); *B01L 2300/0867* (2013.01); *B01L 2300/0877* (2013.01); *B01L 2300/1822* (2013.01); *B01L 2400/0478* (2013.01); *B01L 2400/0487* (2013.01); *B01L 2400/0622* (2013.01); *B01L 2400/0644* (2013.01); *B01L 2400/0688* (2013.01)

(58) Field of Classification Search
CPC .. G06F 19/322; G06F 21/6245; C12Q 1/6827
See application file for complete search history.

(56) References Cited

U.S. PATENT DOCUMENTS

| | | | |
|---|---|---|---|
| 7,851,207 | B1 | 12/2010 | Sagripanti |
| 2001/0051377 | A1 | 12/2001 | Hammer et al. |
| 2003/0005967 | A1 | 1/2003 | Karp |
| 2003/0162304 | A1 | 8/2003 | Dority et al. |
| 2004/0018523 | A1 | 1/2004 | Hawkins |
| 2011/0220502 | A1* | 9/2011 | Selden ............ B01L 3/502715 204/457 |
| 2013/0137169 | A1 | 5/2013 | Kojima |
| 2015/0044758 | A1 | 2/2015 | Amshey et al. |
| 2017/0242963 | A1* | 8/2017 | Cohen .................. G06F 19/322 |

FOREIGN PATENT DOCUMENTS

| | | |
|---|---|---|
| WO | 2016/019476 A1 | 2/2016 |
| WO | 2016/117726 A1 | 7/2016 |

OTHER PUBLICATIONS

Invitation to Pay Additional Fees and Communication Relating to the Results of the Partial International Search, dated Dec. 11, 2017, issued in corresponding International Application No. PCT/GB2017/052855.
International Search Report, dated Jan. 26, 2018, issued in corresponding international Application No. PCT/GB2017/052855.
Combined Search and Examination Report, dated Jun. 13, 2017, issued in priority GB Application No. GB1616174.7.

* cited by examiner

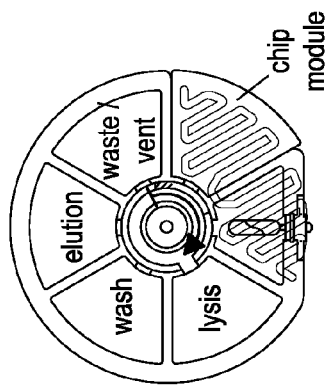
FIG. 12A
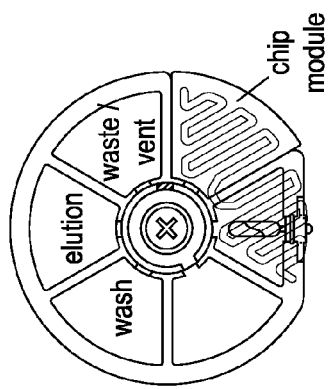
FIG. 12B
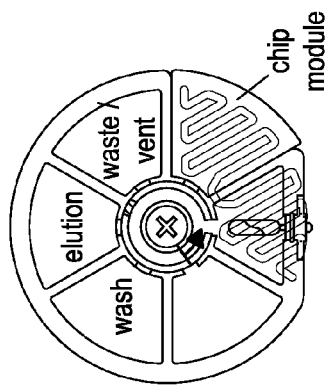
FIG. 12C
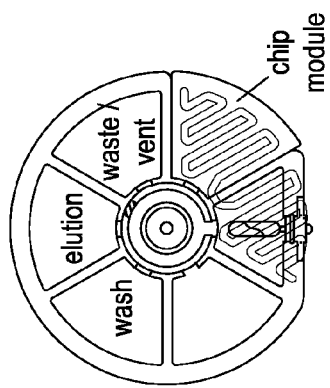
FIG. 12D
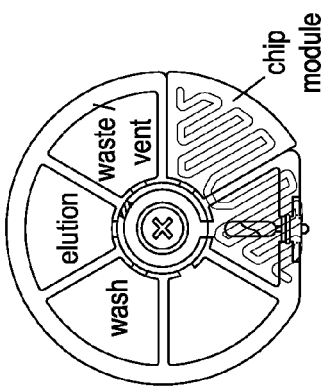
FIG. 12E
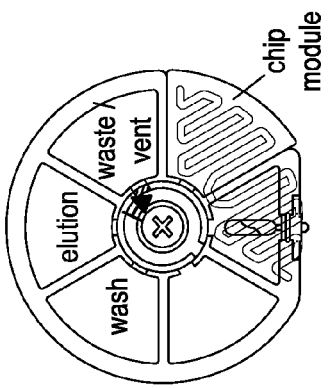
FIG. 12F
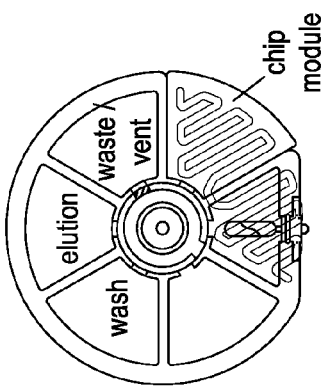
FIG. 12G
FIG. 12H

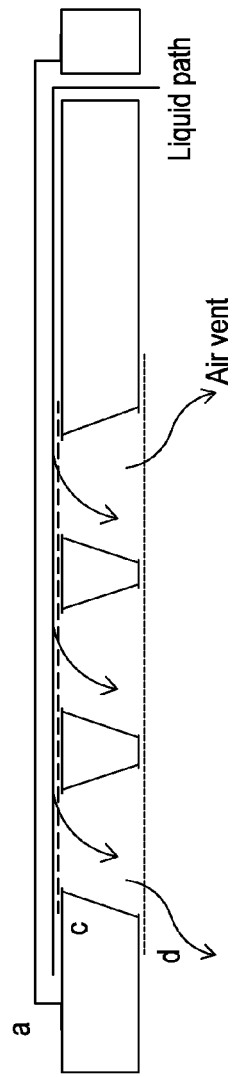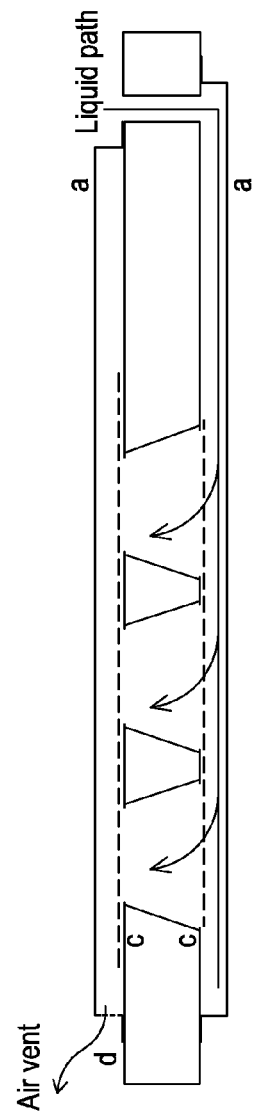

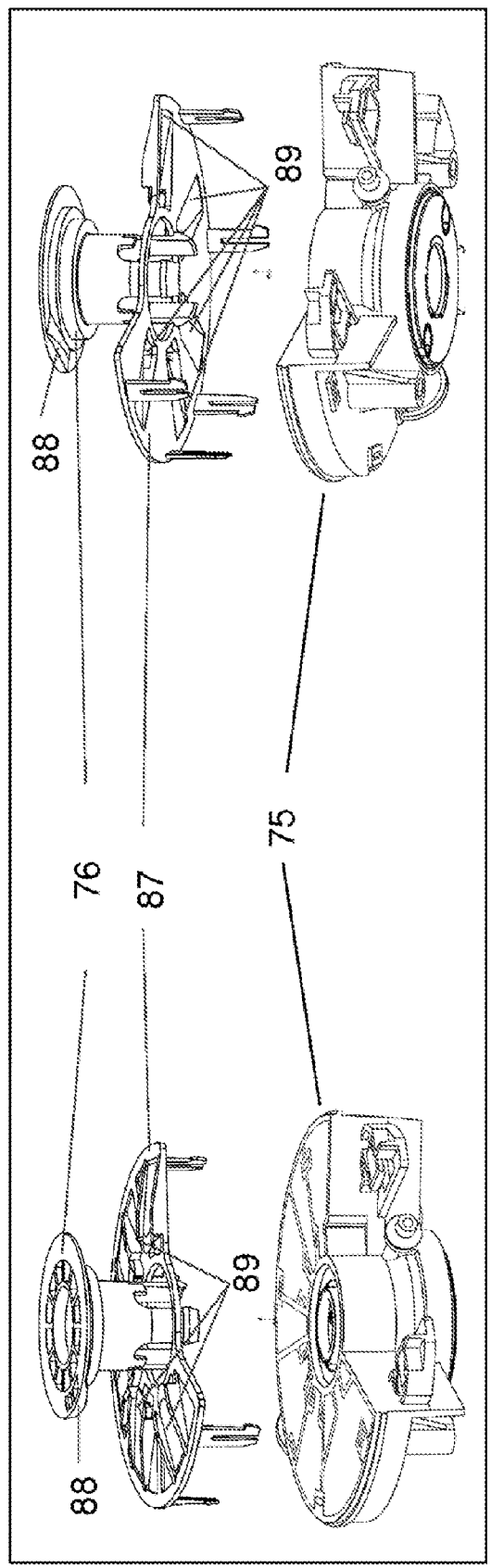
FIG. 28A
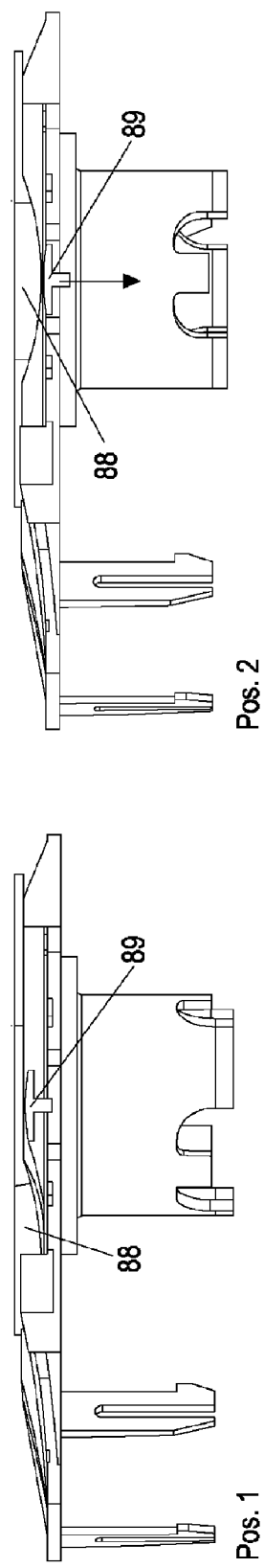
FIG. 28B
FIG. 28C

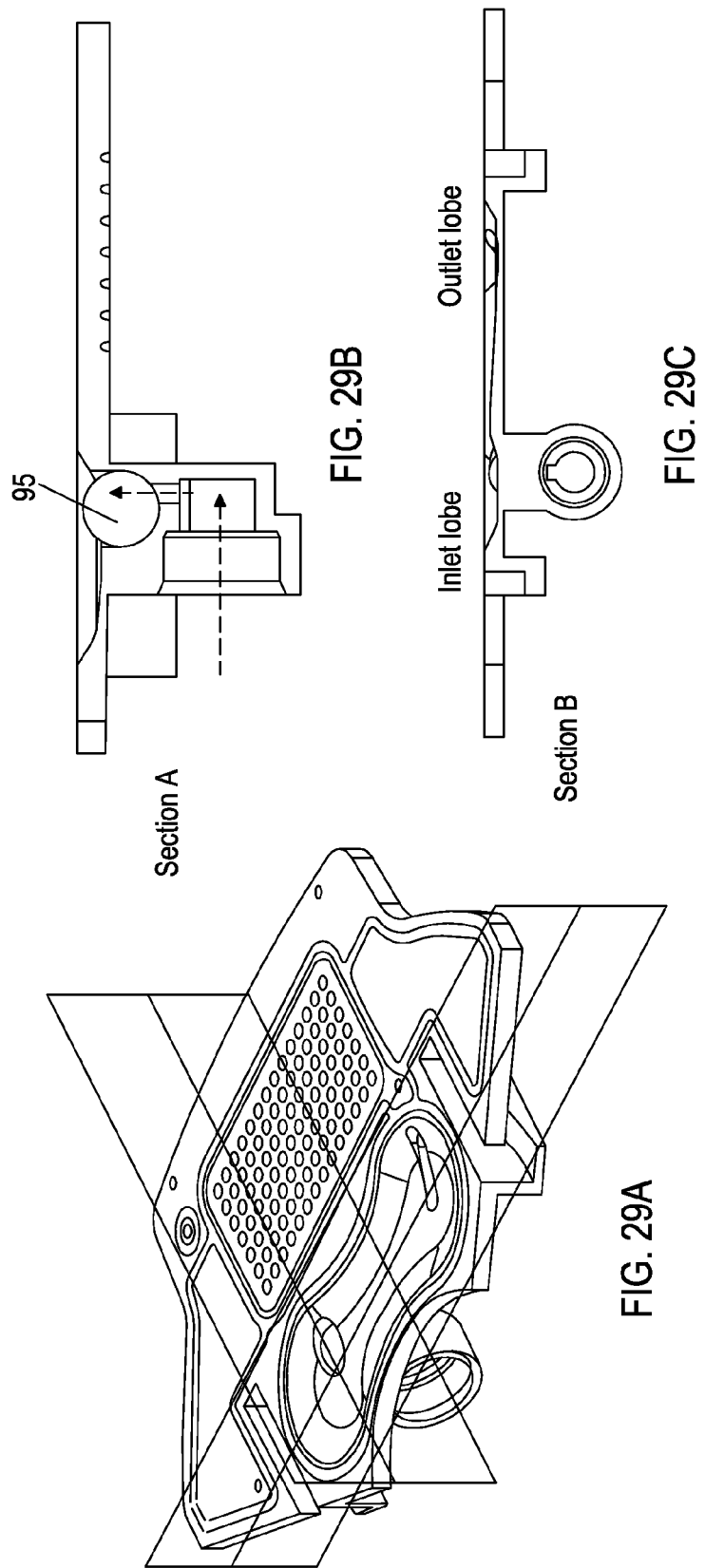

METHOD AND APPARATUS FOR ANALYSING A BIOLOGICAL SAMPLE

CROSS-REFERENCE TO RELATED APPLICATIONS

This application is based on, and claims priority to, UK Application No. 1616174.7, filed Sep. 23, 2016, the entire contents of which being fully incorporated herein by reference.

TECHNICAL FIELD

The present invention relates to a method and apparatus for analysing a biological sample and in particular, though not exclusively, to a method and apparatus for performing Single Nucleotide Polymorphism (SNP) genotyping on a sample of genetic material. The device may also be employed in other assays such as gene expression and simple epigenetic testing. The invention also relates to a method and apparatus for securely storing and using personal genetic and other biological data on a user device.

BACKGROUND OF THE INVENTION

Advances in sequencing technologies and breakthroughs in science have revolutionised the field of genetic data analysis and interpretation, making such services cost-effective and accessible to the general public. Every day, new genetic traits are being described, generating a continuously expanding catalogue of genetic variations that affect the health, wellbeing, and phenotype of living organisms, including humans, animals, microbes, fungi, and plants.

Identifying individual differences at a molecular level has allowed for a deeper layer of personalisation in medicine, such as for drug dosage and treatment selection, as well as in lifestyle improvement and management, by tailoring personal care products ranging from cosmetics and nutraceuticals, to services that enhance fitness, weight-loss regimes etc. A number of private companies have been created in order to cater for this growing consumer genetics market. Nevertheless, limitations in the technologies utilised restrict the commercialisation of such approaches to lab-based services, compromising delivery speed, business models and privacy.

Currently, an individual that wants to gain access to information related to his/her genetics, whether for a specific purpose/concern or for general interest, needs to go through the following process:

1) Order online a sample collection kit from the service provider;

2) Receive the kit and collect the biological sample (usually saliva)—at this stage, the customer may also be asked to fill in a questionnaire that will be analysed together with the genetic results;

3) Send the sample back to the service provider via post; the sample will then be processed by skilled lab staff using various genetic analysis assays; and 4) 4-8 weeks later, the customer will be sent electronically or via post a generic analysis report, listing his/her different variations in the DNA. In some cases, the service provider may make a product recommendation or offer a bespoke product designed or selected according to the client's genetic profile.

These conventional approaches require the customer to send his/her biological sample to some remote location, usually via post, in order to be processed and analysed. This introduces confidentiality concerns with regards to:

1) who analyses the biological sample and how and where this is done;

2) how and where the genetic information is stored, or safely discarded;

3) how is the customer's personal information linked to his/her genetic profile;

4) who can have access to the customer's genetic information;

5) in many cases, prior to releasing the genetic analysis report, the customer is asked to fill in questionnaires in relation to his/her medical history, lifestyle habits etc—sharing such information adds another level of concern.

At this point it should be highlighted that confidentiality concerns are not solely related to the genetic results, i.e. what genetic variants the customer carries, but also relate to the personal concerns that motivated the customer to consider having a genetic test, for instance predisposition to impotence, baldness, drug addiction, alcoholism etc. If this information were to become available to health insurance providers, potential employers etc, an individual could be "genetically stigmatised" and "classified". The impact on an individual life could be enormous.

The majority of the currently available genetic services offer wide genome screening; e.g., using a predefined platform tagged with more than 100,000 biomarkers and screening irrespectively all client samples for all genetic biomarkers. This means that a high proportion of customers are being screened by default for genetic traits that they may not want to know about; for instance, an individual purchasing a test in order to determine his/her predisposition to detoxification will be also screened for serious neurodegenerative diseases such as Alzheimer's and Parkinson's disease. Giving a customer access to information related to concerns that the customer did not initially have, may have a detrimental effect on his or her socio/psychological balance.

A further disadvantage of many of the services available today is that much of the information provided remains greatly un-interpretable and, consequently, of no interest or relevance to the customer's day-to-day life. Whilst some services do offer to the customer personalised services or products, these may compromise the customer's freedom of choice and selection, and they do not take into account an individual's personality and idiosyncrasy, including lifestyle choices, as well as religious, political, and cultural beliefs. For instance, a diet plan high in red meat intake may be recommended for a person who is genetically prone to not absorbing iron, even if the person is vegetarian or simply dislikes red meat. Another example might be a service that provides a tailored personal care product, based on a customer's genetic traits, which has been tested on animals. Such a product, even if specifically designed to the individual's genetic profile, may conflict with his/her views on animal welfare.

Finally, it will be appreciated that in a fast moving world where time is a very important choice-making criterion, the speed with which results are provided is key. The fact that, currently, a biological sample has to be sent off remotely to a laboratory to be processed, means the costumer can be waiting weeks or even months for the results. The longer the time gap between ordering a genetic test and receiving the results/recommended product, the more likely it will be that the customer fails to follow-up with associated purchases.

Taking into consideration the above, it becomes apparent that genetic services that require the sending of biological samples to be processed remotely are often not very attractive from a consumer and/or a business point-of-view, i.e. "do I have a particular condition or trait?", rather than "what actions do I need to take to address a particular trait or condition?". Furthermore, currently genetic results are generally problem-based rather than solution-based. This highlights the desire for services offering genetic testing that a) can be performed by the consumer in his/her own private environment, b) are based on targeted genetic traits due to the customer's specific concerns, c) provide immediate, actionable results, and d) are delivered quickly, reliably, and securely.

The relative complexity and high cost of instruments and procedures for performing SNP genotyping represents a significant barrier to performing tests in a non-technical environment such as the home or a retail premise.

Examples of currently available SNP genotyping systems include those available from Cepheid, Sunnyvale Calif., USA.

Methods and apparatus for analysing and detecting biological samples which utilise the functionality of mobile devices such as smartphones are known. WO2013010178 and WO2014113785 for example describe an instrument with which a smartphone can be docked enabling use of the smartphone's camera to monitor a visual change indicative of a detection event. A related smartphone based system is also considered in "High-Throughput Optical Sensing Immunoassays on Smartphone", Anal. Chem., 2016, 88 (16), pp 8302-8308, Li-Ju Wang et al, and in "Fluorescent Imaging of Single Nanoparticles and Viruses on a Smart Phone', ACS Nano 2013, 7 (10), pp 9147-9155, Qingshan Weri et al.

SUMMARY OF THE INVENTION

According to a first aspect of the present invention there is provided a system for preparing and analysing a sample of biological material. The system comprises a test cartridge having a first housing defining a flow-through chamber, a second housing defining a central space within which the first housing is at least partially located. The first housing is rotatable relative to the second housing, and the second housing defines a plurality of circumferentially spaced chambers, one of the chambers having an inlet for receiving a sample, at least one of the chambers containing a liquid reagent, and at least one of the chambers comprising an analysis module, the chambers of the second housing each having an opening into said central space. The first housing has one or more openings into said central space so that the or each opening can be selectively aligned with one of the openings into the chambers of the second housing by relative rotation of the first housing and second housings.

The system further comprises a base unit having a housing defining or having connected thereto features for docking the test cartridge with the base unit so that the second housing cannot rotate with respect to the base unit whilst the first housing can rotate relative to the base unit. It further comprises a first driver for engaging with said first housing to cause rotation of the first housing within the second housing, a second driver for positively and negatively pressurising the flow-through chamber of the first housing, a controller for operating the first and second drivers to cause displacement of liquids between the chambers in a desired sequence, resulting in the delivery of a prepared sample to the chamber containing the analysis module, thereby facilitating provision of an analysis result by the analysis module. The chamber that contains the analysis module has a transparent window in its upper surface, and said analysis module is configured to provide a visually detectable analysis result that is visible from above the test cartridge through said transparent window.

The chambers of the second housing may be defined in part by a generally cylindrical wall which also defines said central space, the openings of the chambers being provided as openings through the cylindrical wall. The system may further comprise a piston movable axially within the flow through chamber of the first housing, and said second driver cooperating with said piston to positively and negatively pressurise the flow-through chamber.

The second housing may further defines at least one empty chamber for venting or receiving waste liquid, with the test cartridge comprising a third housing fixed beneath the second housing and being in liquid communication with the or each said empty chamber. The third unit may have features defined thereon for cooperating with said features of or connected to the base unit to facilitate docking of the test cartridge with the base unit, the third housing further defining an opening therethrough for alignment with the central space of the second housing so that, when the test cartridge is docked with the base unit, said piston is axially movable through the opening in the third housing into the flow-through chamber of the first housing.

Features for docking the test cartridge with the base unit may be configured to prevent rotation of the second housing with respect to the base unit, a base of the first housing having gear teeth arranged around a circumferential region, said first driver comprising a rotary motor for driving a pinion that is engaged with said gear teeth of the first housing so that rotation of the pinion by the rotary motor causes the first housing to rotate within the second housing. the gear teeth and said pinion may have complimentary bevels so that the pinion sits over the gear teeth. The pinion may have a cut-away section which, when aligned with the gear teeth of the first housing, allows docking and removal of the test cartridge with and from the base unit.

The second driver may comprise a rotary motor and a gear wheel driven by the rotary motor, the gear wheel being coupled to the piston. The piston may comprise a leadscrew axially aligned with the flow-through chamber when the test cartridge is docked with the base unit. The leadscrew may be movable axially but not rotationally with respect to the base unit, the base unit comprising a rotatable threaded nut through which the leadscrew extends, the threaded nut having teeth arranged around an outer circumference and being in engagement with the gear wheel for rotation thereby, rotation of the threaded nut causing axial movement of the leadscrew. the piston may comprise a piston head located within said flow-through chamber and which is engaged by said leadscrew, wherein, prior to docking of the test cartridge with the base unit, the leadscrew is located substantially within the base unit and, following docking, the leadscrew can be extended into the flow-through chamber to engage and capture the piston head.

The system may be configured to perform Single Nucleotide Polymorphism genotyping, and the chambers of the test cartridge comprising at least a chamber containing a lysis buffer, a chamber containing a wash liquid reagent, and a chamber containing an elution reagent. The analysis module may be configured to perform DNA amplification, having an interface to indicate amplification.

The system may comprise features for facilitating docking of a smartphone with the system so that an analysis result of the analysis module can be imaged by a camera of the smartphone.

Said first housing may comprise a porous membrane or other structure within or in liquid communication with said flow through chamber, the porous membrane being configured to retain DNA material. The porous membrane may be a silica frit. The first housing may comprise two or more of said openings into the central space, at least one of the openings being unimpeded and another of the openings being impeded by said porous membrane. The system may be configured such that when one of the impeded and unimpeded openings is aligned with one of the openings into the chambers of the second housing, the other of the impeded and unimpeded openings is not so aligned.

According to a second aspect of the present invention there is provided a system for preparing and analysing a sample of biological material. The system comprises a test cartridge having a first housing defining a flow-through chamber, a second housing defining a central space within which the first housing is at least partially located, the first housing being rotatable relative to the second housing, and the second housing defining a plurality of circumferentially spaced chambers. One of the chambers has an inlet for receiving a sample, at least one of the chambers containing a liquid reagent, and at least one of the chambers comprising an analysis module, the chambers of the second housing each having an opening into said central space. The first housing has two or more openings into said central space so that the or each opening can be selectively aligned with one of the openings into the chambers of the second housing by relative rotation of the first housing and second housings, at least one of said openings being unimpeded and at least one of said openings being impeded by a porous membrane configured to retain DNA material.

The system further comprises a base unit having a housing defining or having connected thereto features for docking the test cartridge with the base unit so that the second housing cannot rotate with respect to the base unit whilst the first housing can rotate relative to the base unit, a first driver for engaging with said first housing to cause rotation of the first housing within the second housing, and a second driver for positively and negatively pressurising the flow-through chamber of the first housing. The base unit further comprises a controller for operating the first and second drivers to cause displacement of liquids between the chambers in a desired sequence, resulting in the delivery of a prepared sample to the chamber containing the analysis module, thereby facilitating provision of an analysis result by the analysis module. The porous membrane may be a silica frit.

The system may be configured such that when one of the impeded and unimpeded openings is aligned with one of the openings into the chambers of the second housing, the other of the impeded and unimpeded openings is not so aligned enabling liquid to flow through only the aligned opening.

According to a third aspect of the present invention there is provided method of providing product recommendations to a user of a mobile device having a camera. The method comprises using a test element to perform a test on a biological sample obtained from the user, the test resulting in a visually detectable change in or on an area of the test element, using the camera of the mobile device to capture an image or images of said area, using a processor of the mobile device to analyse the captured image or images and to identify one or more traits or characteristics of the user, and mapping the traits or characteristics to a plurality of products in order to obtain a personalised recommendation for each product. The method further comprises maintaining a database of products, recommendations, and product machine readable codes or other product identifying information in the mobile device, using the camera to scan a machine readable code or product identifying information on a product, using the scanned code or product identifying information to determine a recommendation for the product by way of the database, and presenting the recommendation to the user via a user interface of the mobile device.

The method may comprise docking the mobile device with an instrument configured to perform said test prior to the step of using the camera and, subsequent to that step, removing the mobile device from the instrument to facilitate said step of using the camera to scan a machine readable code or product identifying information on a product.

The test may be a Single Nucleotide Polymorphism (SNP) genotyping test, and said step of using a processor of the mobile device to analyse the captured image or images and to identify one or more traits or characteristics of the user comprises mapping one or more SNP genotypes to one or more traits or characteristics and associating those traits or characteristics to the user.

The method may comprise selecting a test element of a test element type associated with an area of interest of the client, using the mobile device to determine the chosen test element type, and using the identified type to identify one or more traits or characteristics of the user. The steps of using a processor and mapping the traits or characteristics, may comprise communicating between the mobile device and one or more servers via a communication network such as the Internet.

According to a fourth aspect of the present invention there is provided module for analysing a sample of biological material. The module comprises a base member defining an inlet for receiving a liquid containing said sample of biological material or a component derived from said sample of biological material, a trough in liquid communication with said inlet, and an array of wells in which an analysis is performed. The module further comprises a sheet fixed to an upper surface of the base unit to define a first space above said trough and a second space above said wells, the sheet being transparent at least in a region above said second space, the base member further defining a channel to transfer liquid from said first space to said second space.

The module may comprise a lyophilized material located between said inlet and said trough and configured to dissolve on contact with liquid. The trough may have a double-lobe shape, said inlet communicating with an opening into a first of the lobes and said channel opening into a second of the lobes. The module may define a venting space beneath the wells and a hydrophobic membrane secured between the bottoms of the wells and said space to allow air to escape from the wells whilst substantially preventing the escape of liquid. It may comprise one or more biomarkers fixed to said hydrophobic membrane at locations aligned with the bottoms of the wells.

Each said well may be defined by one or more sloping sidewalls such that each well is narrower at the top than at the bottom.

The module may comprise an air and liquid permeable membrane secured to the tops of the wells to partially isolate the wells from said second space and one another, with said air and liquid permeable membrane being substantially transparent.

According to a fifth aspect of the present invention there is provided module for analysing a sample of biological material. The module comprises a base member defining an inlet for receiving a liquid containing said sample of biological material or a component derived from said sample of biological material, and an array of wells in which an analysis is performed. The module defines a space adjacent said array of wells and into which the wells open, the space being in liquid communication with said inlet, the module further comprising a hydrophobic membrane fixed to the array to separate the wells from said space. The module may comprise a flexible sheet, impermeable to both air and liquid, fixed to said base member to define said space.

The wells may open into a second space on an opposite side to said first space, a hydrophobic or hydrophilic membrane being fixed over the array to separate the wells from said second space. The module may further comprise a hydrophobic membrane fixed between the first mention hydrophilic membrane and the array.

It will be appreciated that the module described above comprises numerous novel features including the well shapes, membrane properties and locations, venting features, microfluidic structures and functions etc. all of which may be used separately or in various combinations. It is not intended here to limit the invention to any one of these.

According to a sixth aspect of the present invention there is provided a test cartridge for analysing a sample of biological material and comprising, or being configured to receive, a module according to the fourth or fifth aspect of the invention. The test cartridge comprises an outer housing defining a plurality of chambers and a central space, and an inner housing located in said inner space and defining a flow through chamber, the inner housing being rotatable within the outer housing. The outer housing may define openings from said central space into respective chambers, and a further opening in communication with said module.

The outer housing may define a first substantially frustoconical surface aligned with an axis of rotation of the inner housing, and said inner housing defining a second substantially frustoconical surface abutting said first substantially frustoconical surface, said openings being provided in the first substantially frustoconical surface and an opening into said flowthrough chamber being defined in said second substantially frustoconical surface, the test cartridge being configured to allow alignment of the opening into the flowthrough chamber with any one of the openings defined in the outer housing. The test cartridge may comprise a seal or seals for sealing the openings defined in the outer housing against said second substantially frustoconical surface of the inner housing. It may further comprise a biasing member for urging the first and second substantially frustoconical surfaces against one another.

The test cartridge may comprise a flexible membrane or membranes covering the chambers of the outer housing, the test cartridge further comprising a component axially movable relative to the outer housing in order to pierce the membrane or membranes and vent them to the surrounding environment. Said component may be configured to move axially relative to the outer housing upon rotation of the inner housing.

BRIEF DESCRIPTION OF THE DRAWINGS

FIGS. 11A-11C, 12A-12H, 13A-13D, 14A-14D and 15 illustrate the introduction of a sample into the test cartridge of FIG. 1 using a buccal swab;

FIGS. 25A and 25B illustrate schematically a well array area of the cartridge of FIG. 19 showing a first mechanism for achieving well filling;

FIGS. 26A and 26B illustrate schematically a well array area of the cartridge of FIG. 19 showing a first mechanism for achieving well filling;

FIGS. 28A, 28B and 28C illustrate a chamber piercing component that can be optionally added to the cartridge of FIG. 19;

FIGS. 29A, 29B and 29C include a top perspective view of the cartridge of FIG. 19 and two orthogonal cross-sectional views;

DETAILED DESCRIPTION OF THE INVENTION

A system will now be described that is suitable for use in a non-technical environment such as the home or a retail premise. As such, it aims to offer a relatively small footprint, be available as a relatively low cost system, and be operable by a non-technical person such as a consumer or shop assistant. Of course, this does not exclude the use of the system in a technical environment and indeed there will be many advantages in doing so.

Figure 1:
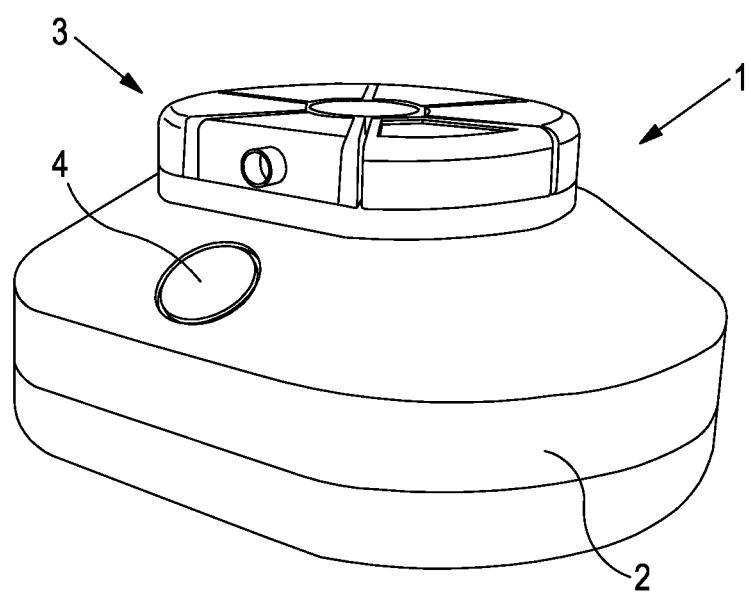
FIG. 1 illustrates a system comprising a base unit and test cartridge for performing SNP genotyping on a biological sample.

FIG. 1 illustrates an exemplary SNP genotyping system 1 comprising a base unit or instrument 2 and a test cartridge 3 docked with the base station. Whilst the former component is intended to be reusable many times, the latter component is intended to be single use and disposable. The test cartridge is configured to be clipped into the base unit as will be described further below. For the purposes of illustration only, a button 4 is shown incorporated into the base unit 2. With the test cartridge clipped into the base unit, a user can initiate a test by depressing the button 4.

Figure 2B:
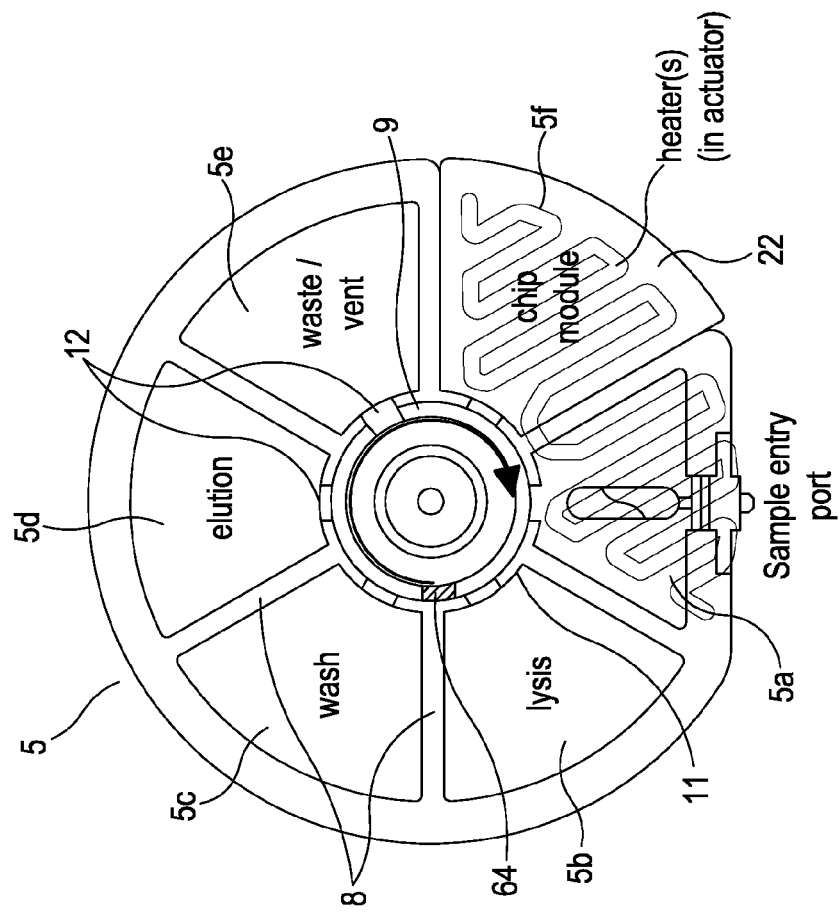
FIGS. 2A and 2B illustrate exploded views of the test cartridge of FIG. 1 together with a plan view of the cartridge identifying various compartments thereof.
Figure 2A:
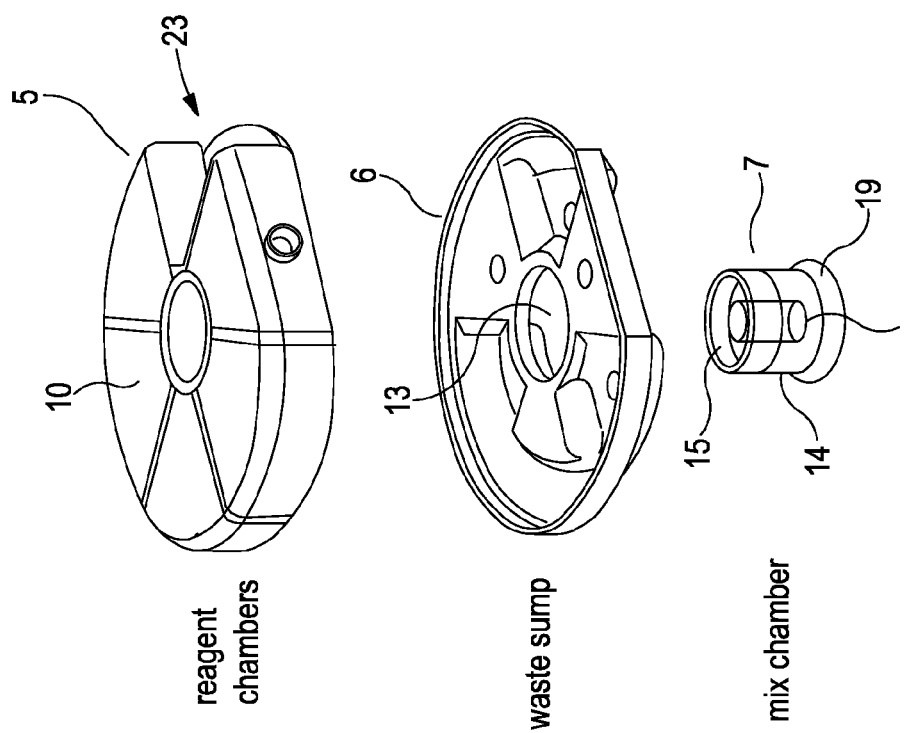

FIGS. 2A and 2B show exploded views of the test cartridge 3 from which is can be seen that the cartridge comprises an upper, multi-chamber unit 5, a lower unit 6 which provides a waste sump and into which the upper housing is clipped, and a rotating chamber 7. From the plan view shown in the Figure, it can be seen that the interior of the upper unit 6 is subdivided into six chambers 5a-f by radially extending walls 8. The upper unit provides a central interior space 9 defined by a closed upper surface 10 and a cylindrical wall 11 of the upper unit. The space 9 is therefore generally cylindrical, being open at its lower end. Each of the chambers 5a-f is in liquid communication with the interior space 9 via an associated radially extending hole in the cylindrical wall 11 (one of these holes is indicated in the Figure by reference numeral 12).

As will also be apparent from the Figure, a circular opening 13 is provided in the lower unit 6 which, in the assembled test cartridge, is aligned with the lower opening into the interior space 9 of the upper unit 5. The upper and lower units are constructed of a suitable polymer such as Polypropylene, PTFE or COC. Advantageously, the upper unit may be made of a transparent polymer to allow a user to view certain steps in the analysis process.

Figure 3:
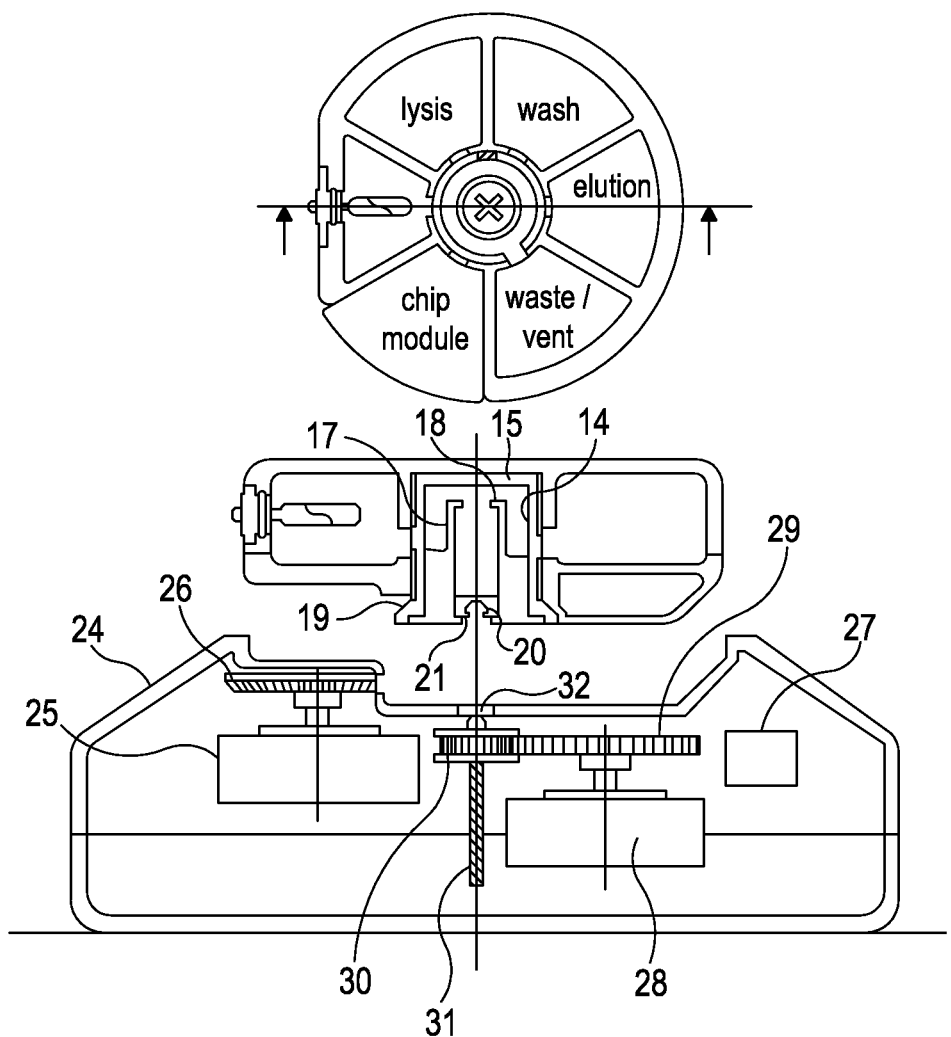
FIG. 3 illustrates a docking procedure and orientation for the cartridge with the base unit.

The rotating chamber 7 comprises a generally cylindrical member 14 defining an interior (flow through) space closed by an upper wall 15. This is best seen in FIG. 3 and in the subsequent Figures. Whilst the upper wall 15 closes the space completely, a circular opening 16 is provided in the base of the cylindrical member 14. A cylindrical wall 17 extends upwardly from the base of the cylindrical member 14, within the interior space. This separates the interior space into a cylindrical space within the cylindrical wall 17, an annular space surrounding the cylindrical wall 17, and a cylindrical space between the top of the cylindrical wall 17 and the upper wall 15 of the cylindrical member 14. An inwardly protruding lip 18 surrounds the upper circumference of the cylindrical wall 17. A bevelled gear "wheel" 19 is formed around the lower, outer periphery of the rotating chamber 7 such that the teeth of the gear wheel face in a generally upward and outward direction.

A plunger head 20 of rubber (or a material having similar properties) is installed within the rotating chamber so as to be movable up and down within the space defined by the cylindrical wall 17. The plunger head 20 forms a substantially airtight and water tight seal within the cylindrical wall 17. The plunger head 20 is provided at its lower end with a capture feature 21.

As shown in the Figures, a pellet of silica fibres/particles ("frit") 64 is pressed into the rotating chamber such that liquid entering the chamber will contact the frit. Specifically, and by way of example only, the frit is shown pressed into an opening into the rotating chamber so that, when the opening is aligned with an opening into one of the chambers of the upper unit, liquid is caused to flow through the frit. The silica material provides a large area surface for selectively binding DNA via chaotropic-salt-induced adsorption at high salt concentrations, and to avoid the adsorption of proteins, lipids, carbohydrates, and RNA. The role of the elution agent (see below) is therefore to decrease the salt concentration and release the bound DNA. Use of a silica frit to bind DNA is described in "Driving Forces for DNA Absorption to Silica Perchlorate Solutions", Kathryn A. Melzak et al, Journal of Colloidal and Interface Science, 181, 635-644 (1996). Alternatively, the DNA can be captured on silica-coated magnetic particles, and prevented from leaving the rotating chamber by collecting on a side wall under the application of a magnetic field. An example system using magnetic particles and magnetic fields to bind DNA is ChargeSwitch, available from Thermo Fisher, Waltham Mass., USA.

In the assembled test cartridge 3, with the upper unit 5 clipped securely into the lower unit 6, the rotating chamber 7 extends through the opening in the lower unit into the interior central space 9 of the upper unit, forming an interference fit with the cylindrical wall 11 of the upper unit. The fit is such that the rotating unit is able to rotate within the upper and lower units.

Referring again to the plan view of the test cartridge shown in FIGS. 2A and 2B, the six chambers 5a-f of the upper unit 5 are configured to participate in various stages of a sample analysis procedure. In this example, the test cartridge is suitable for performing Single Nucleotide Polymorphism (SNP) genotyping on a sample of genetic material obtained from a person or animal. As will be well known to the person of skill in the art, SNP genotyping involves detecting which of a number of genetic variations is present at each of one or more SNPs of a person or animal's genome. These SNP variations can provide markers to a condition or trait of the person or animal whose genome is being analysed. In order to perform SNP genotyping, the chambers 5a-f are configured as follows:

Chamber 1/Sample chamber (5a): The input chamber which receives the sample, e.g. by insertion though an inlet port of a buccal swab. The chamber is provided with a heater which is under the control of device controller (see below).

Chamber 2/Lysis chamber (5b): Contains a lysis buffer. In SNP genotyping, the lysis buffer is provided to break up the cell membrane and release the subject's DNA.

Chamber 3/Wash chamber (5c): Contains a wash liquid reagent. This may be, for example, ethanol.

Chamber 4/Elution chamber (5d): This chamber contains an elution reagent to remove DNA from the solid phase such as de-ionised water or 10 mM Tris pH 8.5.

Chamber 5/Waste-Vent chamber (5e): This chamber is empty prior to use, and is in liquid communication with the lower unit 6 (waste sump).

Chamber 6/Analysis chamber (5f): This chamber contains a chip module which is configured to perform amplification and sequencing. By way of example, the chip may use an ISFET-based detection system such as that developed by DNAe, London, UK. The chip module comprises various components including filled reagent chambers, microfluidics, a heater or heaters, and control electronics.

In the illustrated example, the analysis chamber is actually formed as a separate, self-contained component 22 which is plugged into an open segment 23 of the upper unit 5. This configuration may provide increased flexibility as the upper unit 5 can receive different chip modules depending upon the test to be performed. Also, as the chip modules may have a shorter shelf-life than the assembled upper unit, the latter may be stockpiled in larger quantities with the chip modules being plugged in close to the intended time of use. Of course, the chip module may be formed integrally with the rest of the upper unit 5.

Referring now to FIG. 3, this shows a cross-section taken vertically through the base unit 2. The base unit comprises an outer housing 24 defining a substantially closed interior space. The upper surface of the housing 24 and the lower surface of the lower unit 6 have complimentary features to allow for full insertion of the test cartridge 3 into the base unit 2 in only a single rotational orientation.

Only certain components are shown mounted within the housing 24, and it will be appreciated that others are also present including those discussed further below. The illustrated components include a first rotary motor 25 connected to a bevelled pinion 26. The bevelled pinion 26 is provided with a cut-away section to allow the test cartridge 3 to dock flush with the top surface of the base unit 2. In order to allow insertion of the test cartridge 3 into the base unit 2, a controller 27 of the base unit ensures that the bevelled pinion 26 is rotated to a position in which the cut-away section faces towards the centre of the unit. This is the configuration shown in FIG. 3. When the test cartridge is in the correct orientation, it can be lowered into the base unit without interference with the bevelled pinion 26.

Figure 4:
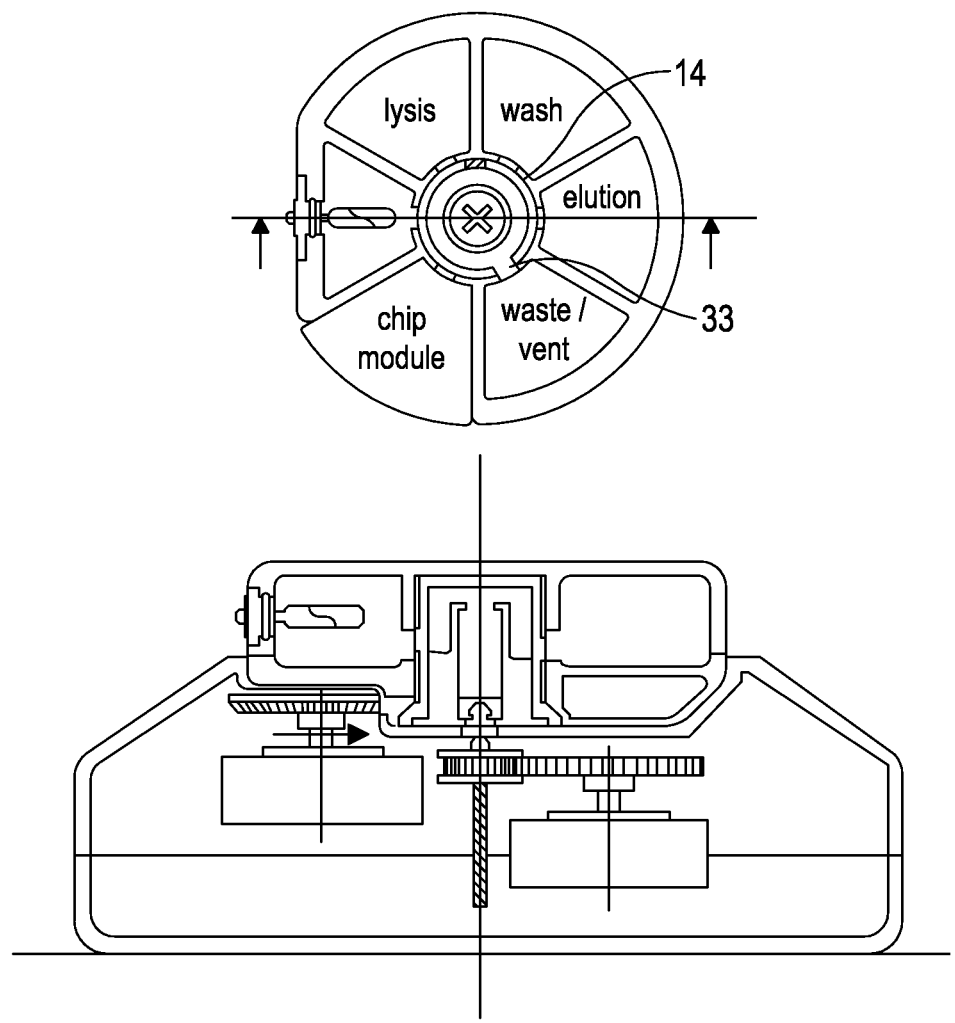
FIG. 4 illustrates the system of FIG. 1 with docked test cartridge and instrument in a locked, start configuration.

It will be readily appreciated that a small rotation of the bevelled pinion 26 will cause it to move over the complimentary bevelled gear wheel 19 formed around the rotating chamber 7, resulting in engagement of the bevelled pinion with the gear wheel. Any further rotation of the bevelled pinion 26 will result in rotation of the rotating chamber 7 within the upper and lower units which are held in place, rotationally, by the engagement of the lower unit with the base unit housing. As long as the bevelled pinion 26 is engaged with the gear wheel 19 any upward force applied to the test cartridge is resisted. This state is illustrated in FIG. 4. The gearing ratio between the pinion 26 and the gear wheel ensures that the rotation chamber can be rotated through more than 360 degrees by rotation of the pinion despite the pinion cut-away.

With further reference to FIG. 3, the base unit 2 can be seen to comprise a second rotary motor 28 connected to a first gear wheel 29. The first gear wheel 29 meshes with a second gear wheel 30 which is in threaded engagement with a lead screw 31 passing coaxially through the second gear wheel 30. The lead screw 31 is provided with a capture head 32. Rotation of the motor spindle in a first direction results in the lead screw 31 moving up, whilst rotation in the opposite, second direction, will result in the lead screw moving down. Both the first and the second motor are controlled by the controller 27 which may be, for example, a digital processor with memory for storing control code (power for all components may be provided by an on-board battery or via a ac/dc power inlet). In the state where the test cartridge 3 is docked with the base unit 2, the controller is in electrical or wireless communication with one or more components of the test cartridge, for example, with heaters and with a processor of the chip module 22. The controller 27 also provides a means to communicate with some external monitoring/analysis system. In one embodiment, the controller may be able to communicate wirelessly with a user's smartphone, e.g. using a Bluetooth™ or WiFi™ wireless interface. Alternatively, there may be a wired communication interface such as USB, etc. The controller may also be able to receive instructions via the same interface.

The system described here provides a great deal of flexibility when it comes to moving liquids between chambers and containing liquids within chambers. The following features are of particular interest and may be employed independently or in combination:

It is possible to receive a liquid from a chamber of the upper housing and contain it within the rotating housing for a desired period of time (thereby isolating a reaction step). The rotating chamber can be rotated such that no openings of the chambers of the upper housing align with the opening into the rotating chamber.

Multiple reagents to be mixed together at a specified point in the protocol (in cases where it not desirable for the reagents to be stored mixed together for long periods of time—or in the case where a dilution is required). This can be carried out in the rotating chamber or one or more of the chambers of the upper housing.

The provision of a solid phase (silica frit) inside the rotating chamber means that the chamber is not merely a simple 'reagent transport' element, but rather becomes an active functional participant in the process.

The interaction of the piston with the rotating chamber provides for a mixing action to be incorporated, e.g. by pumping liquids between the rotating chamber, a chamber of the upper housing, and back again.

The interaction of the piston, when not fully extended, may be used to dispense less than 100% of the volume between rotating chamber and a chamber of the upper housing, and vice versa.

The rotating chamber may be provided with two or more openings. Indeed, the example illustrated in the Figures includes two such openings. These are spaced circumferentially to selectively align with openings in the chambers of the upper housing.

By way of example, a few steps of an exemplary operating sequence will now be described.

Figure 5:
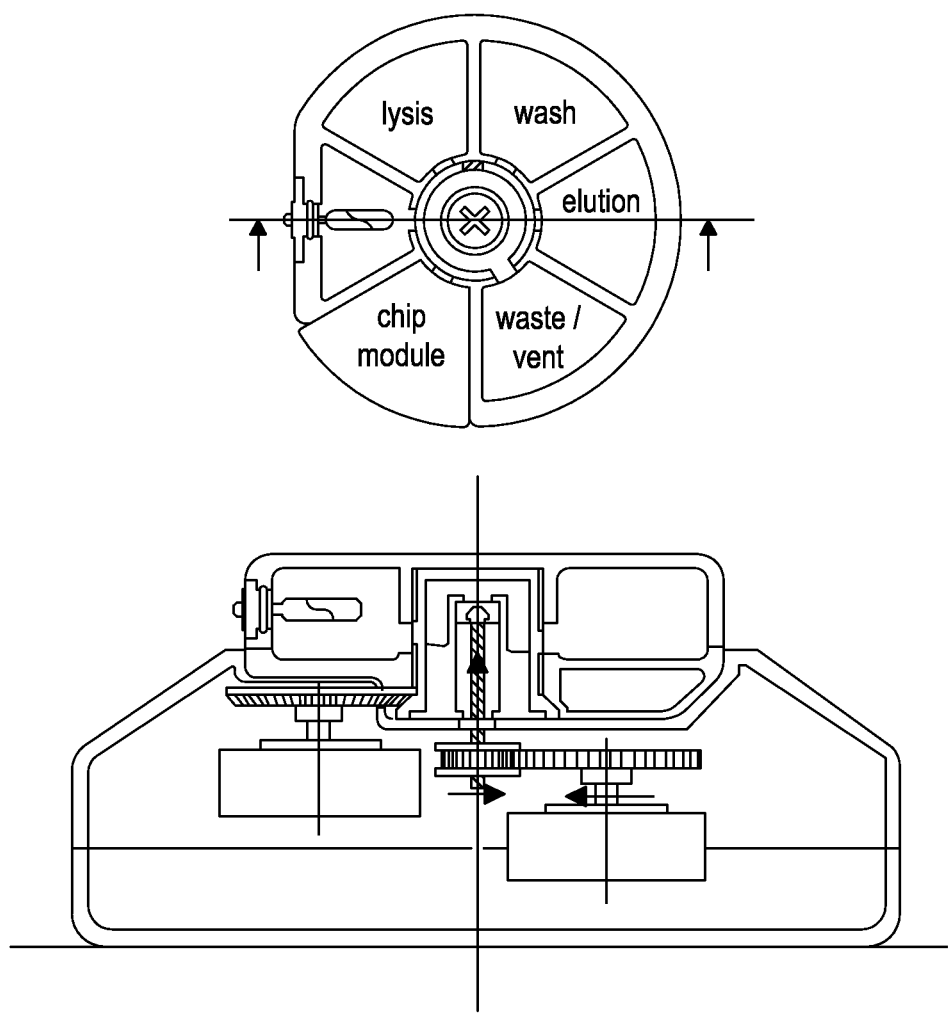
FIGS. 5 to 9 illustrate the system of FIG. 1 in various operational states.

As already noted, FIG. 4 shows the test cartridge 3 engaged with the base unit 2, with the bevelled pinion 26 having been rotated to engage the bevelled gear wheel 19 of the rotating chamber 7. In this orientation, a radially extending opening 33 formed in the cylindrical member 14 (of the rotating chamber 7) is aligned with the hole 12 into a waste/vent chamber 5e. The second motor 28 is now operated to cause the lead screw 31 to extend upwards. The upward motion of the lead screw causes the capture head 26 to contact and move upwards the plunger head 20 within the rotating chamber 7. The upwards motion of the plunger head causes air to be expelled from the rotating chamber through the vented static chamber. As the plunger head 20 reaches a hard stop provided by the lip 18, the capture head 32 of the lead screw is pushed into the complimentary capture feature 21 formed in the base of the plunger head. This configuration is shown in FIG. 5.

Although not shown, the base unit can be provided with a heater or heaters to raise the temperature of reagents within chambers. Increasing the temperature can improve the yield of DNA extracted from a sample.

Figure 6:
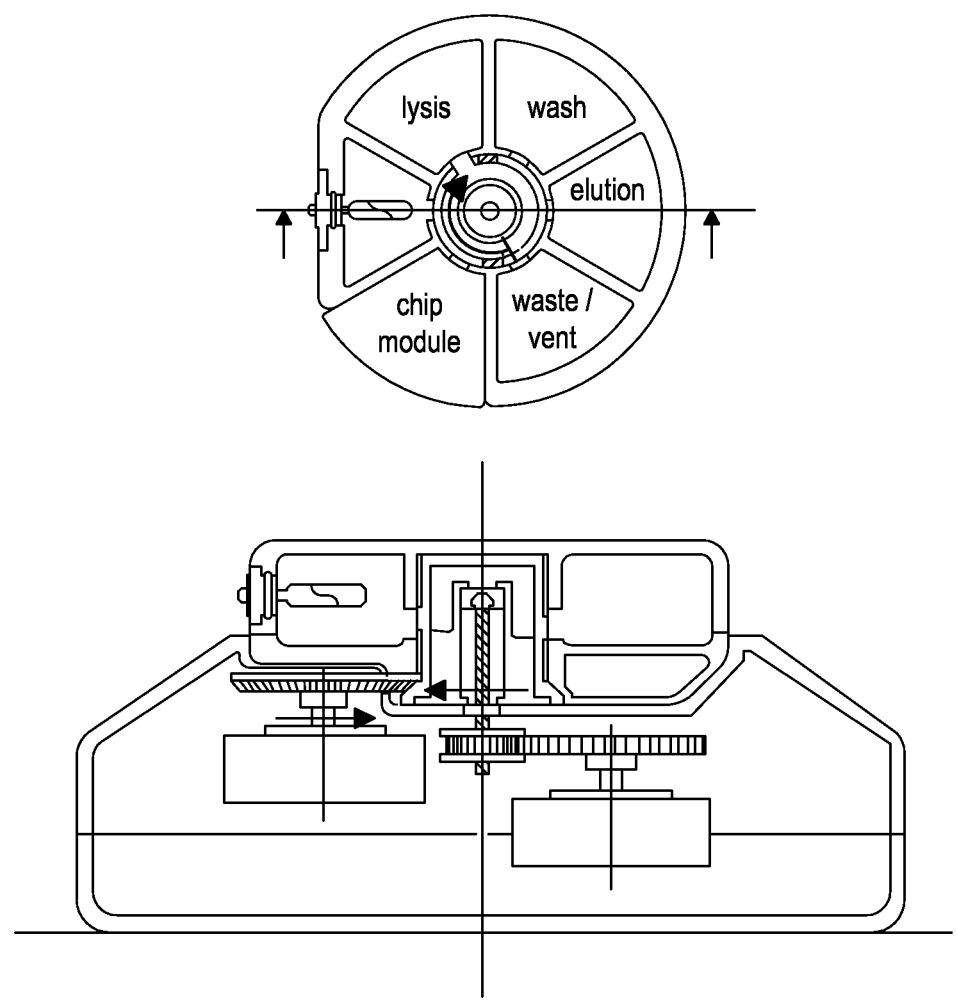
Figure 7:
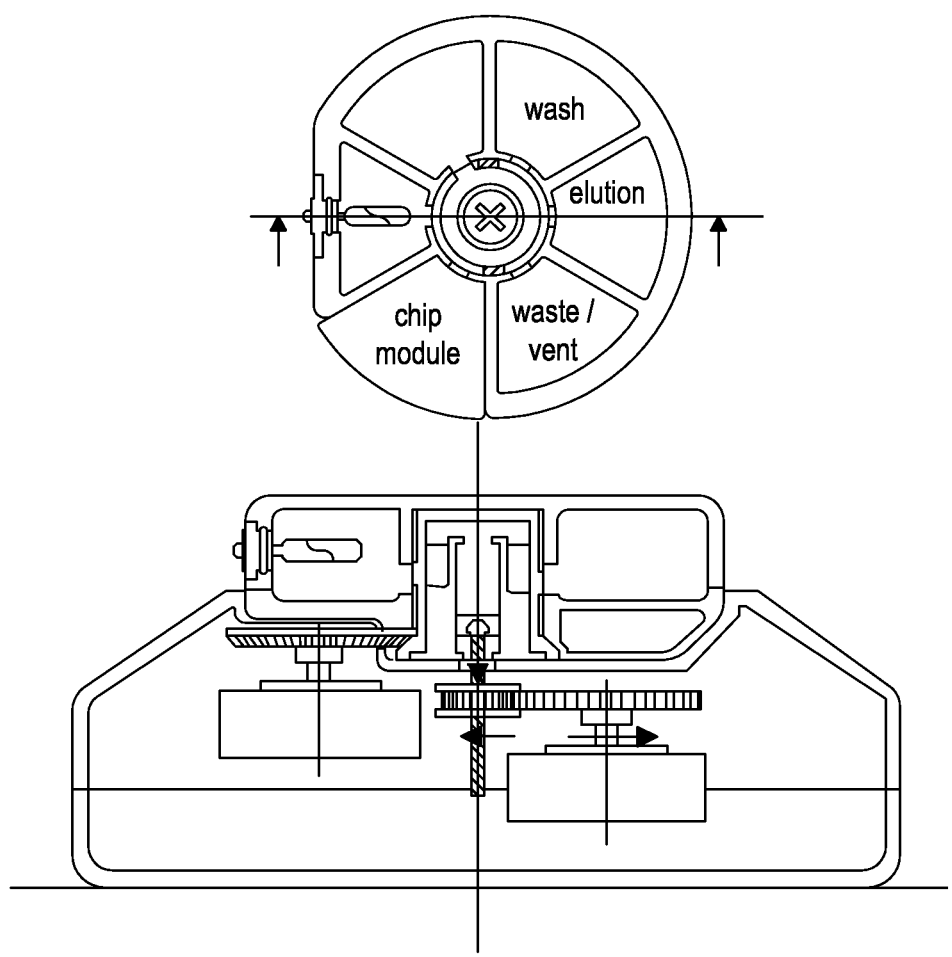

Referring now to FIG. 6, the bevelled pinion 26 is rotated to turn the rotating chamber 7 so that the opening 33 into the rotating chamber is aligned with the hole 12 leading into the lysis chamber 5b. The lead screw 31 is then caused to withdraw downwards by rotating the second motor 28. This configuration is shown in FIG. 7 from which it can be seen that the downward motion of the lead screw has caused the plunger head 20 at the base of the rotating chamber 7 to be translated downwards by means of the capture head 32. The downwards motion of the plunger head 20 generates negative air pressure causing liquid to be drawn from the lysis chamber 5b into the annular space defined within the rotating chamber 7.

It will be clear from FIG. 7 that liquid fills only the annular space within the rotating chamber 7, and does not overflow into the cylindrical inner space within which the plunger head 20 and the lead screw 31 move. The upwardly extending cylindrical wall 17 therefore acts as a "weir", preventing contamination of the inner space and importantly of the lead screw and capture head. This ensures that no contamination of base unit occurs allowing its reuse with further test cartridges.

Figure 8:
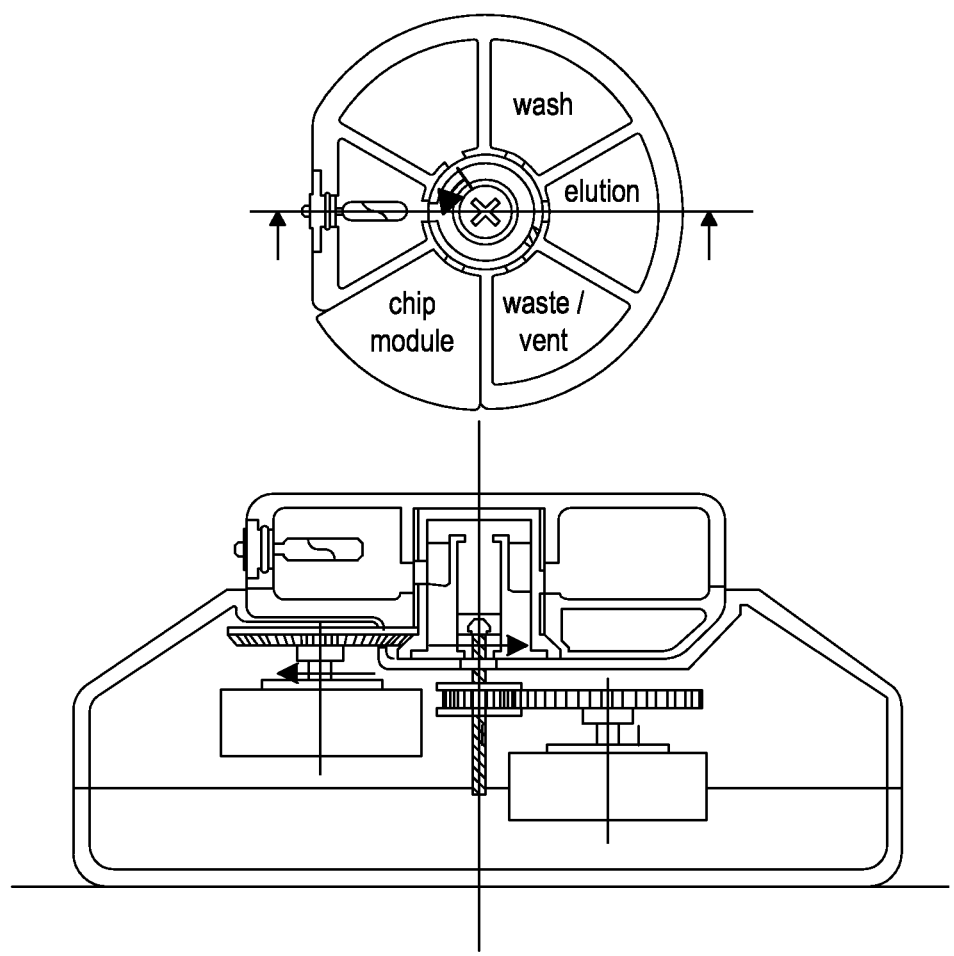
Figure 9:
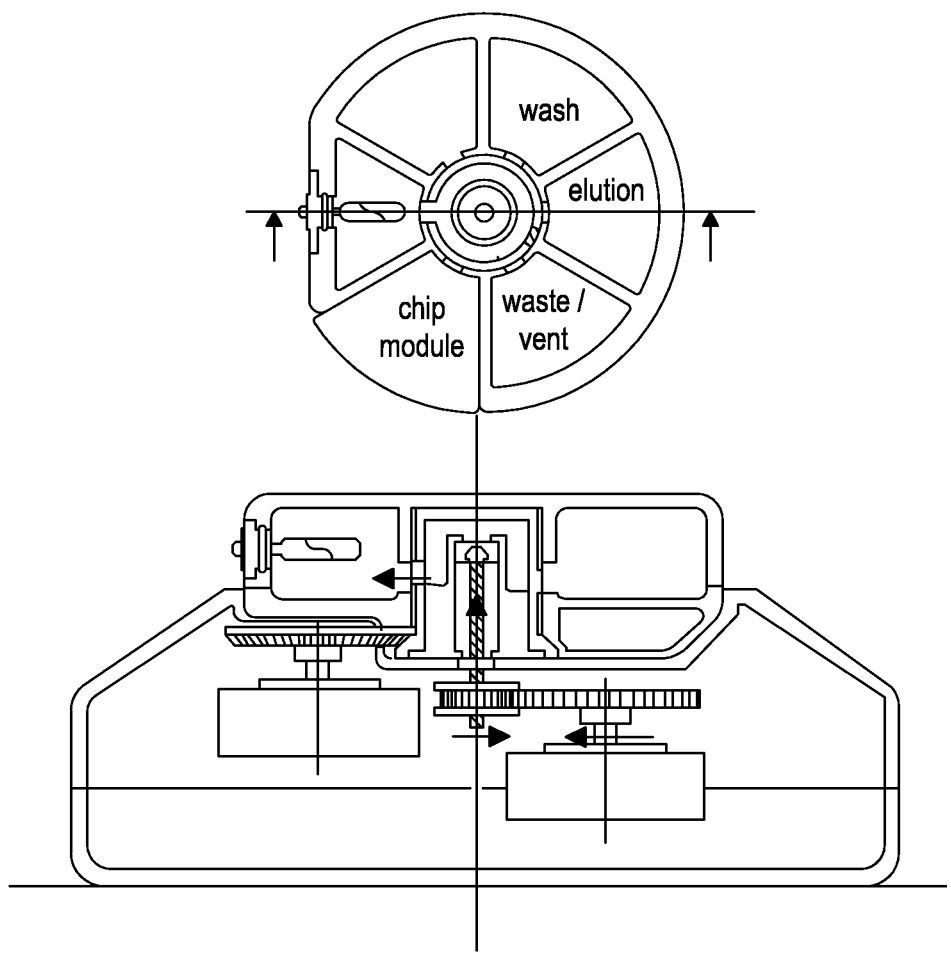

As shown in FIG. 8, the bevelled pinion 26 is now rotated to turn the rotating chamber 7 so as to align its opening 33 with the opening 12 into the sample chamber 5a. The lead screw 31 is then caused to extend upwards by rotating the second motor 28. The upward motion of the lead screw causes the plunger head 20 to be translated upwards within the rotating chamber 7. The upwards motion of the plunger head generates positive air pressure causing lysis liquid to be expelled from the rotating chamber 7 into the sample chamber 5a. This is shown in FIG. 9.

It will be understood from the above discussion that workflows for sample processing can be built by sequentially combining rotations of the rotating chamber and movements of the plunger to transfer reagents from the rotating chamber 7 to the static chambers 5a-f and vice versa, and to transfer reagents between static chambers via the rotating chamber.

Figure 10:
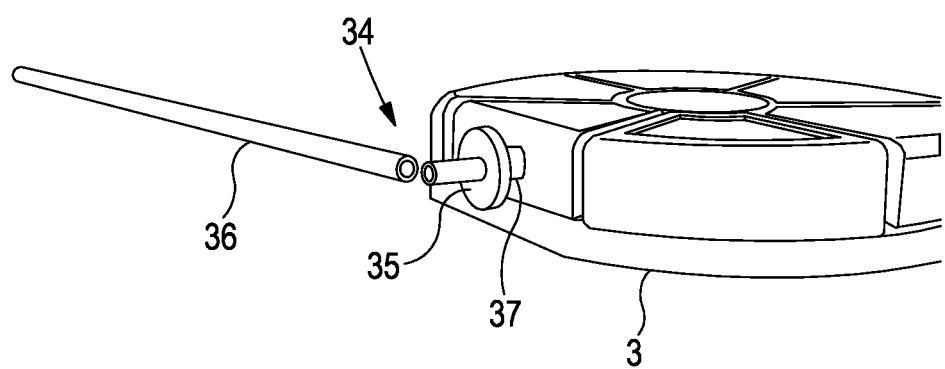
FIG. 10 illustrates schematically a number of stages in the processing of a sample using the system of FIG. 1.

FIG. 10 illustrates the use of a buccal swab 34 to introduce a sample into the test cartridge. The collection end 35 of the swab is pushed into an access port 37 provided in the outer wall of the sample chamber 5a. Once the collection end of the swab is fully inserted, the user snaps off the handle 36.

Figure 11C:
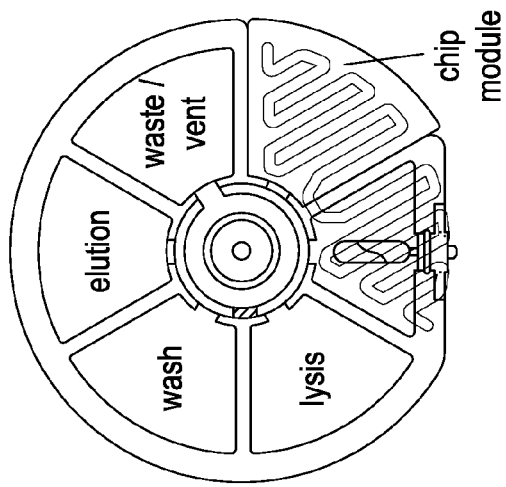
Figure 11B:
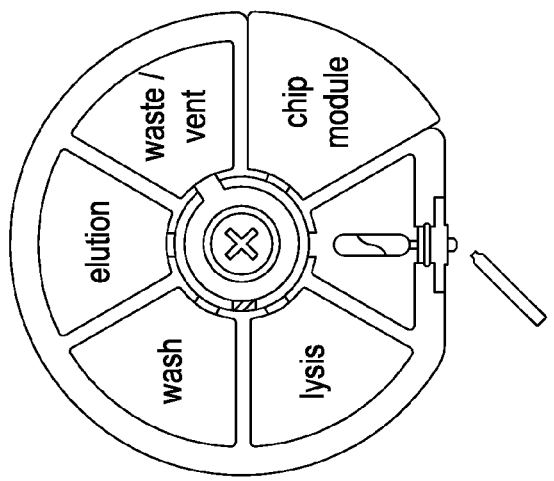
Figure 11A:
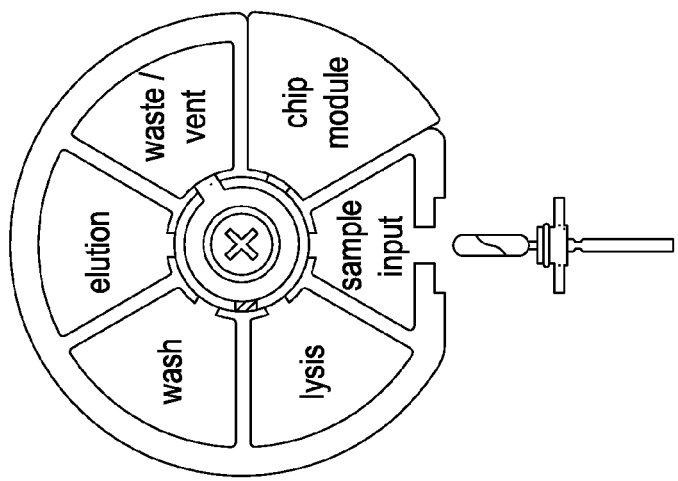
Figure 13A:
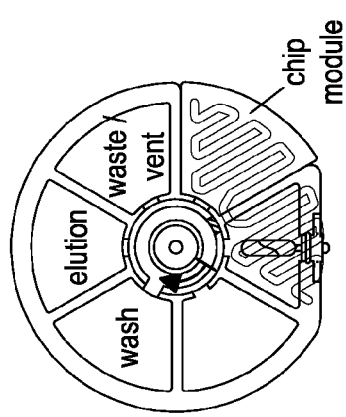
Figure 13B:
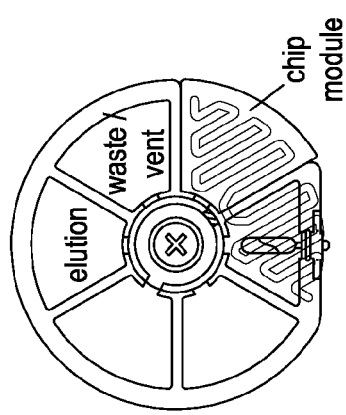
Figure 13C:
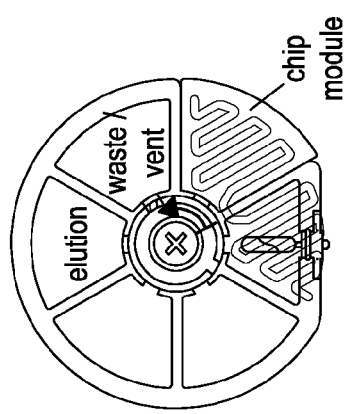
Figure 13D:
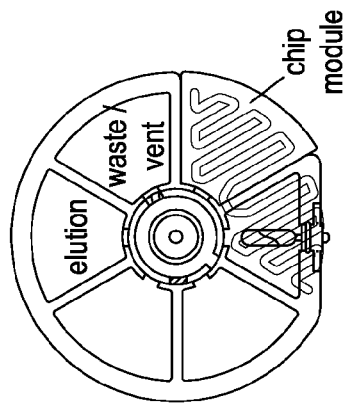
Figure 14A:
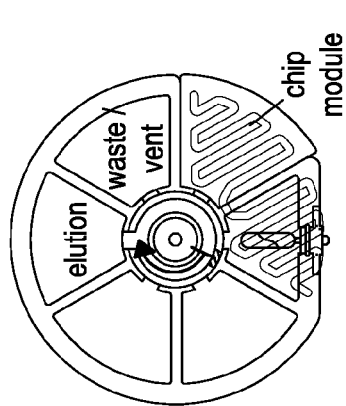
Figure 14B:
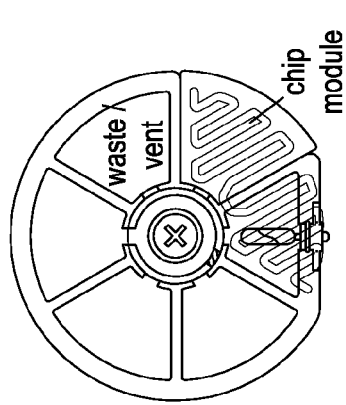
Figure 14C:
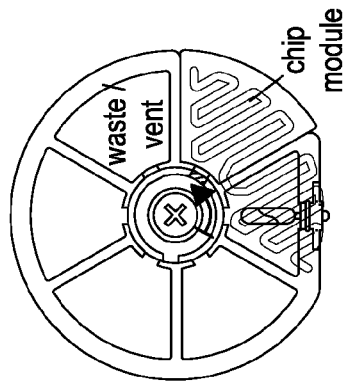
Figure 14D:
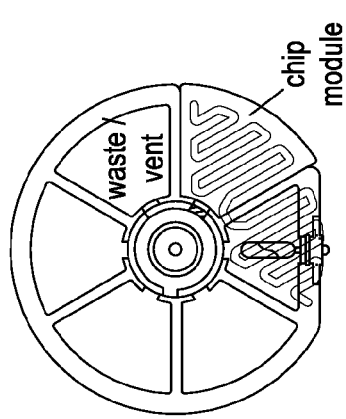

In one embodiment, illustrated in FIGS. 11A-11C, 12A-12H, 13A-13D, 14A-14D, and 15, the workflow for sample processing is as follows, assuming the use of a buccal swab to collect a sample of genetic material:

Input—The sample head is introduced into the sample chamber. The head is snapped off to seal the sample chamber. The sample processing system is placed on the base unit. The rotating chamber is vented to air. FIGS. 11A-11C.

Lyse—The rotating chamber is rotated to connect to the chamber containing the lysis reagent. The lysis reagent is transferred from the reagent chamber to the rotating chamber. The rotating chamber rotates to connect to the sample chamber. The lysis reagent is transferred from the rotating chamber to the sample chamber. The reagent in the sample chamber is heated to an elevated temperature to help remove DNA from the cell interior. The lysis reagent containing DNA is transferred from the sample chamber to the rotating chamber. The rotating chamber rotates to connect to the waste chamber. The lysis reagent containing DNA contacts the DNA collection material. The supernatant is transferred from the rotating chamber to the waste chamber. FIGS. 12A-12H.

Wash—The rotating chamber is rotated to connect to the chamber containing the wash reagent. The wash reagent is transferred from the reagent chamber to the rotating chamber. The rotating chamber rotates to connect to the waste chamber. The wash reagent contacts the DNA collection material. The supernatant is transferred from the rotating chamber to the waste chamber. FIGS. 13A-13D.

Elute—The rotating chamber is rotated to connect to the chamber containing the elution reagent. The elution reagent is transferred from the reagent chamber to the rotating chamber. The rotating chamber rotates to connect the frit containing opening to the analysis chamber. The elution reagent passes through the DNA collection material (porous frit), releasing DNA into solution. The elution reagent containing DNA is transferred from the rotating chamber to the analysis chamber. FIGS. 14A-14D.

Figure 15:
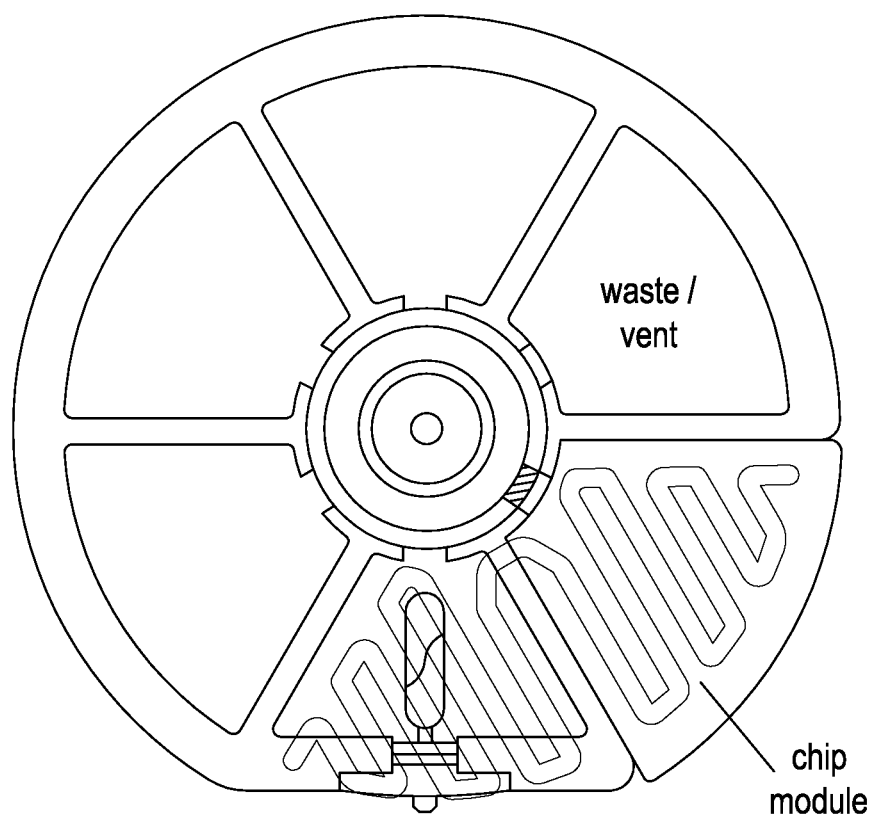

Amplify—The elution reagent containing DNA is heated to elevated temperatures to amplify the DNA therein. The amplification might employ one of a number of known different methods of isothermal or thermal cycling (such PCR). A plurality of primer and probe sets may be present at each aliquot of the chip module, designed to operate at the specified DNA amplification protocol. For an optimum operation (for example in terms of efficiency and speed) the primers might be designed in a way to generate short amplicons. FIG. 15.

In the embodiment described above, the analysis chamber is provided by a chip module which relies upon electrochemical detection mechanisms, e.g. ISFET-based sensors.

An analysis chamber of the test cartridge may make use of electrochemical-based detection techniques (such as those available from Genmark Dx, Carlsbad Calif., USA), or may make use of thermal stability of matched probe-target versus mismatched probe-target as a detection technique.

In an alternative implementation, the analysis chamber makes use of fluorescence-based detection techniques. For example, the process may use intercalating dye, e.g. SYBR Green or as described in the Internet publication:

http://www.bio-rad.com/webroot/web/pdf/lsr/literature/Bulletin_10014647.pdf.

An alternative approach involves the use of a probe-based approach, e.g.

https://www.thermofisher.com/uk/en/home/life-science/pcr/real-time-pcr/real-time-pcr-assays/snp-genotyping-taq-man-assays.html.

The exemplary SNP genotyping system 1 described above employs two openings into the rotating chamber 7, one unimpeded and the other impeded by the silica frit 64. However, more or fewer openings may be employed. For example, an embodiment may employ only a single opening into the rotating chamber, that opening being impeded by a silica frit.

Figure 16:
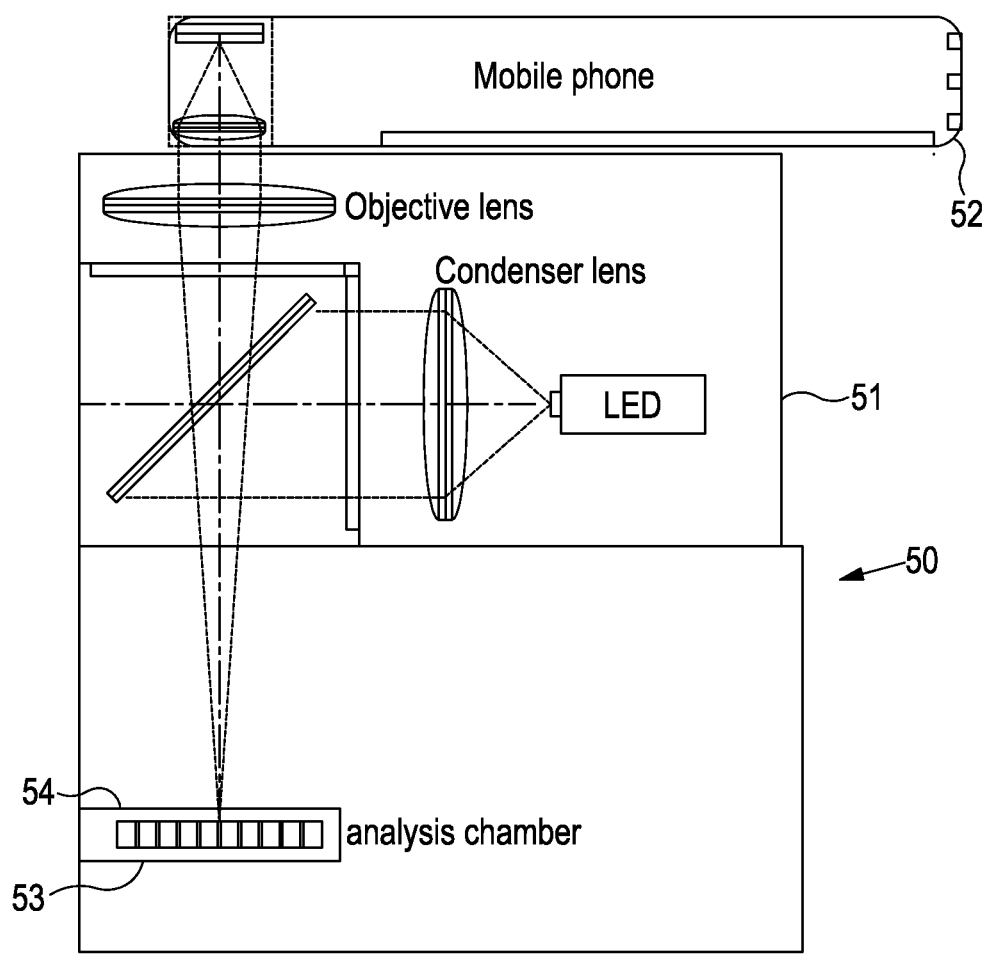
FIG. 16 illustrates an alternative base station configuration into which a user's smartphone is docked.

Such systems require an imaging mechanism such as a camera. Whilst the camera may be integrated into the base unit, arranged to capture an image of a part of the analysis chamber (e.g. through a transparent window), an attractive alternative is to allow for the docking of an external user device with the base station, where the user device has its own camera and associated processing components. FIG. 16 illustrates an example system in which a base unit 50 is provided with a smartphone docking station 51. A user's smartphone 52 is docked with the base station via the docking station. A test cartridge 53 is shown inserted into a cartridge reception port 54 of the base unit.

The test cartridge and base unit of this second embodiment have similar functionality to the respective components of the first embodiment, although modification is required in order to allow visual access to the analysis chamber. Of course the skilled person will be readily able to realise changes in the style and form of the system without changing the fundamental operating principles.

Considering now the docking station 51, this comprises optics or at least a line of sight to optically couple a camera on the underside of the smartphone 52 with the analysis module at least when the test cartridge has been rotated to an optical detection position. The docking station and optics may provide for use with a number of different smartphones having different shapes and sizes and camera positions, e.g. using adjustable optics and or adaptors of differing configurations.

The docking station may include an electromechanical interface to enable two-way communication between the base unit and the smartphone: for example, a Lightning™ male connector port may be used to interface with an iPhone™. Alternatively, the smartphone and the base unit may communicate wirelessly.

By making use of an analysis control app (software application) installed on the smartphone, the smartphone may be used to control the operation of the base unit and therefore the analysis process. Imaging data captured by the smartphones camera may be analysed within the smartphone and or by making use of a service in the "cloud".

As already noted above, user privacy is of critical importance when it comes to offering personalised genetic-based services, not only because of the real threat of data leaking to unscrupulous parties, but also because of the need to ensure that users trust the services and are therefore willing to make use of them. Conventional personalised genetic-based services such as that offered by 23andme™ rely on users sending samples of their genetic material to a remote facility where analysis is performed and the results interpreted, before the results are returned to the users. Despite privacy safeguards, users are wary of such services as the results and analysis are to a large extent beyond their control. Embodiments of the present invention, such as that illustrated in FIG. 16, can be used to address this problem.

Consider a personalised genetic-based service which aims to provide advice and recommendations to users across a range of different categories. These categories might include nutrition (possibly divided into more refined sub-categories such as weight loss, allergies, intolerances, etc), exercise, sleep, etc. For each of these categories, one or more SNPs are identified which can be used to classify user traits. Many examples of categories, SNPs, and traits are known from the scientific literature and more are being identified on an almost daily basis. Analysis chambers 5f, such as a chip module, are configured for each category of the service. In other words, an analysis chamber used for the nutrition category is configured to test for the SNPs relevant to nutrition. The other chambers of the test cartridge may be configured for this specific analysis chamber if it is not generic to all analysis chamber types. In the case that the analysis is to be performed in a retail premise such as a supermarket or department store, a user may purchase a suitably configured test cartridge from a range of available cartridges. For use in the home, test cartridges may be purchased via a web shop and delivered to the user's home, or purchased in a store and brought home for use.

To perform an analysis, the user inserts the purchased test cartridge into the base unit and docks his or her smartphone. The user then opens the relevant app on the smartphone (assuming that it has been pre-installed). The app detects automatically that the smartphone is docked. Some form of authentication may be performed on the test cartridge. For example, the camera may be used to read a barcode or other machine readable code present on the test cartridge. Authentication can be performed using some algorithm available to the app and/or by communicating with the cloud. Alternatively, authentication may rely on communication between the test cartridge and the base station, optionally involving the smartphone.

Once authenticated, the user can initiate the test by tapping on a "button" presented on the smartphone's touchscreen. Of course, the app may be configured to provide any suitable form of graphical user interface, menu selection, etc. Via the docking station, the smartphone communicates with the base unit, causing it to operate the first and second motors, heaters, etc, in order to carry out the various steps of the SNP genotyping procedure. At appropriate time points during the procedure, a signal is sent to the smartphone to cause the smartphone to operate its camera. Although in some cases only a single image may be captured upon completion of the test, by capturing multiple images throughout the procedure specificity to the test result may be enhanced.

The app is provided with algorithms to process and analyse the captured image(s). Again, this may make use of processing within the cloud. If the cloud is used, then data exchanged between it and the smartphone is secured using encryption. Furthermore, data may be anonymised to prevent any direct association between the data and the user. The result of the analysis may be a set of user-specific traits. These traits may in turn be mapped to a set of recommendations. In the case of nutrition, assuming a sub-category of weight loss, the set of recommendations may comprise a database of food products each mapped to a recommendation. The database is loaded into the smartphone app, e.g. by downloading it from the cloud.

Considering this example further, the database of food products may include, for each product, a barcode matching the barcode used on the product packaging. Databases of product barcodes are widely available, e.g. from supermarkets etc. The app on the smartphone is enabled with a barcode reader which makes use of the built-in camera. After the test has been completed and the database installed (or updated) in the smartphone, the user can use the smartphone/app to scan a product barcode before or after purchase. The app will recognise the product and indicate the personalised product recommendation. For example, the user may be advised, via the smartphone GUI, that the product is recommended for weight loss or is inadvisable. The app may even recommend a similar, alternative product that is preferred. The app may be configured to encourage or "nudge" the user to change their purchasing/consumption behaviour, rather than trying to enforce a change. This might include for example the use of rewards, financial or otherwise.

Whilst it is known to use a smartphone to capture and analyse the results of a genetic-based test, and it is separately known to use a smartphone to capture product barcodes and provide product advice, there is a surprising synergy from combining these two features into the same device. This lies in the ability to contain personalised data within a single user controlled, and therefore user trusted, device. Subject to the use of the cloud, which again can be controlled by the user, raw test data is read into the smartphone via the camera, analysed there, and the results retained within the smartphone. As product barcodes are read directly into the smartphone using its camera, the analysed data can be applied to the products wholly with smartphone. Of course, assuming that the app is appropriately configured, the user may choose to share his or her personalised data with third parties and further devices. In one embodiment, the smartphone may share data with a wearable device such as a fitness (wrist) band, with the wearable device having its own barcode reader. Product barcodes may be read by the wearable device, data exchanged between the smartphone and the wearable device, and product recommendations provided either by the smartphone or the wearable device. Assuming that the communication between the smartphone and the wearable device is via a secure link under the user's control, e.g. via a Bluetooth™ interface, the user retains control of his or her personal data at all times. Embodiments of the invention overcome clear technical problems arising with previously known systems and methods, namely the need to send personal and sensitive genetic data outside of the user device (smartphone).

Figure 17:
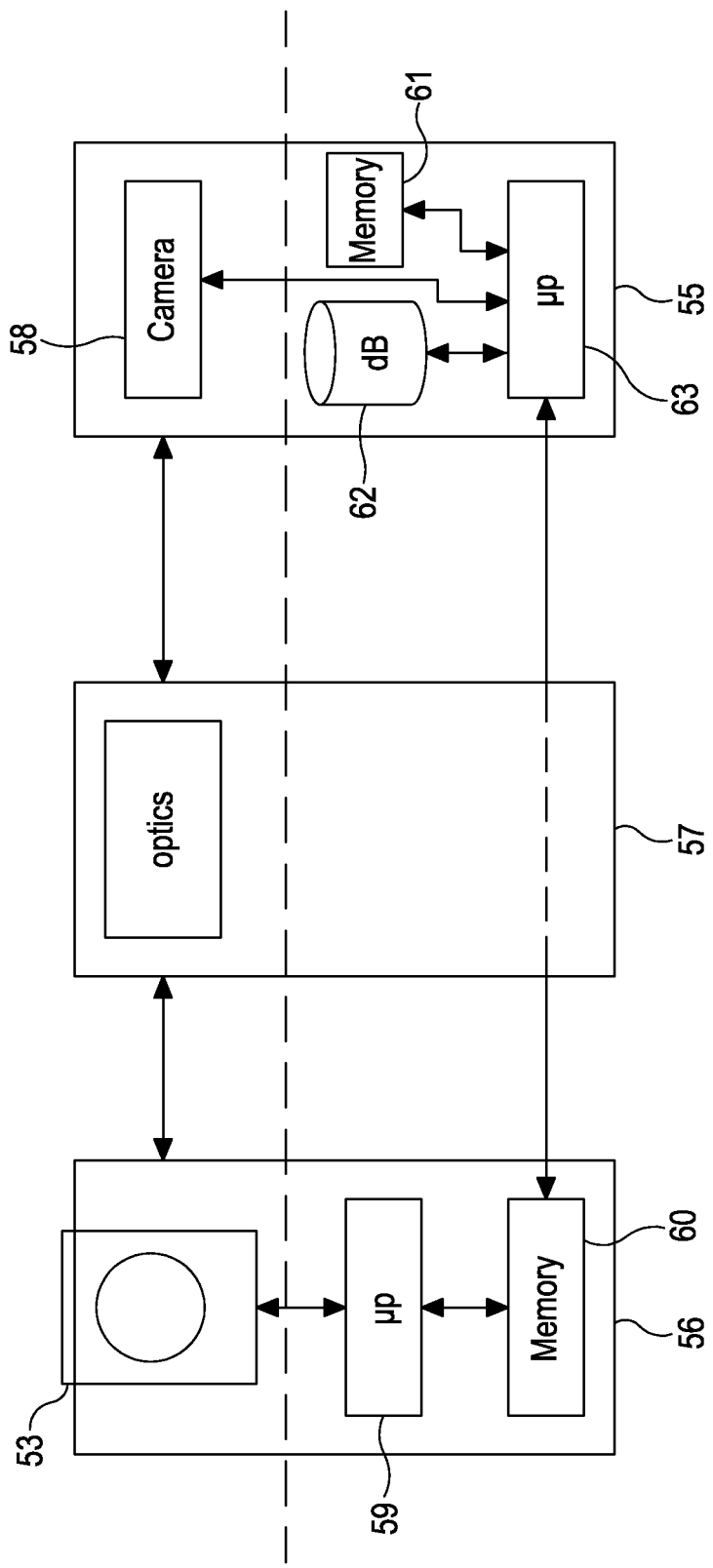
FIG. 17 illustrates schematically an architecture for providing product recommendations incorporating the base station and smartphone of FIG. 16.

FIG. 17 illustrates schematically a system configured to operate in accordance with this approach. A user smartphone 55 is docked with an instrument 56 via docking compartment 57 of the instrument. The docking compartment comprises optics to direct the smartphone's camera 58 onto a result area of a test cartridge held in the instrument. As discussed above, the test instrument comprises a controller 59 which communicates with the smartphone and controls operations performed within the instrument. The instrument also comprises a memory 60 which may store both code for execution by the processor and data, e.g. parameter data and result data. The smartphone comprises a specially configured processor, e.g. configured using code stored in a memory 61, which detects docking of the smartphone and operates the camera to capture a result image. The processor may also determine a cartridge type, i.e. identifying the nature of the test being performed, e.g. relevant to nutrition, exercise etc. The processor further analyses a captured image to map the results to a user characteristic or trait. For example, in the case of an allergy type cartridge/test, the processor may determine from the result image that the user has a nut allergy.

The smartphone is operated by a microprocessor 63 and maintains a product database 62, e.g. listing all products stocked by a particular supermarket. The database includes, for each product, an associated barcode. When a test has been performed and the user characteristics/traits determined, the database is populated with determined product recommendations. In the aforementioned allergy example, entries for all products containing nuts may be tagged with a recommendation "do not purchase". When the smartphone is removed from the dock and a product barcode subsequently scanned, the product database within the smartphone may be inspected to determine the corresponding product recommendation. The recommendation can then be presented to the user, e.g. via the display, and audible signal, vibration alert, etc. Of course, the smartphone may be configured to communicate with one or more network servers via, for example, the Internet, in order to delegate part of the processing operation to the server or servers, and/or to obtain current data.

It will be appreciated by the person of skill in the art that various modifications may be made to the above described embodiments without departing from the scope of the invention. For example, embodiments may use mobile devices other than smartphones to interface with the base unit, e.g. a smart watch, fitness band (Fitbit™), etc. Whilst the embodiments described above have been concerned with SNP genotyping, the inventive concepts may be applied to other methods of testing biological samples including but not limited to testing of RNA, components of a person's microbiome, testing plants, fungi, etc.

Examples of alternative methods for detecting biomarkers and suitable for use with embodiment of the invention include: Conductivity/pH, Electrochemical, Refractive index, End point, Thermal stability. Examples of other amplification methods include Isothermal and Thermal cycling. Examples of other readouts (other than SNP) include RNA profile, DNA methylation.

Figure 18:
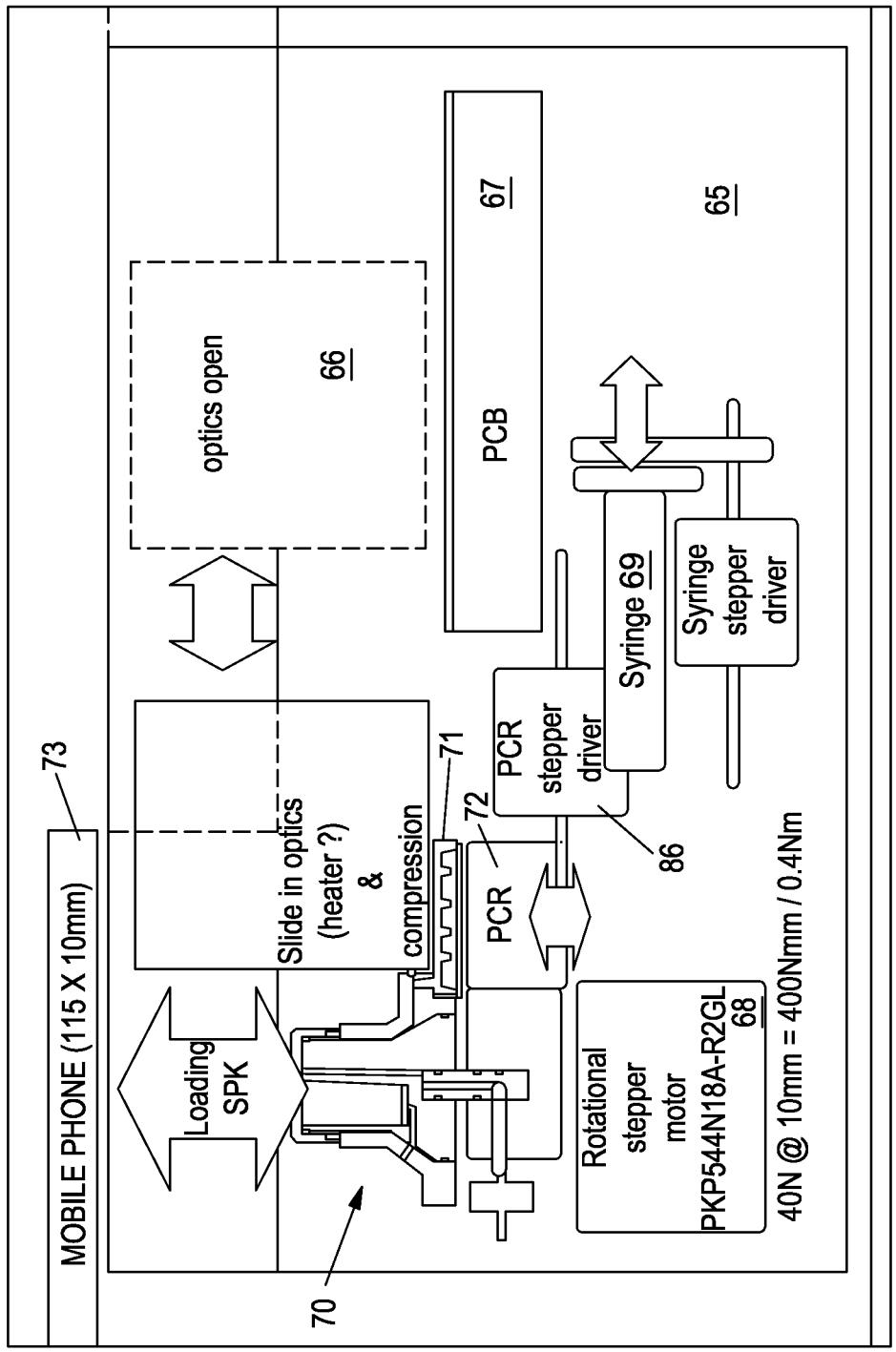
FIG. 18 illustrates schematically an alternative system for performing SNP genotyping on a biological sample.

FIG. 18 illustrates schematically an alternative system for use with a user's smartphone to detect SNPs in a sample of genetic material. The system again comprises a base unit 65 and in which are located a number of components including optics 66, a PCB 67, a rotational stepper motor 68, and a syringe 69. In this system, the optics 66 can be slid to the right (as viewed in the Figure) to allow a test cartridge 70 (only part of which is shown in the Figure) to be inserted into the base unit from above. Once inserted, the optics are slid to the left so that they sit above the analysis chamber 71 of the test cartridge. The system is then initialised, causing a PCR stepper driver to press a Peltier module 72 (used to perform PCR) upwards against an under surface of the analysis chamber 71. As the optics cannot move in the vertical direction, the analysis chamber is squeezed between the Peltier module and the optics, forcing liquid into the wells of the analysis chamber (further details are presented below).

In a further modification to the previously described system, rather than using a plunger located in the flow through chamber (FIG. 3), the syringe 69 within the base unit 65 is configured to apply positive or negative pressure to the flow through chamber within the test cartridge via a series of communicating channels. This is described further below.

FIG. 18 illustrates a smartphone 73 docked with the base unit 65 such that a camera of the smartphone sits directly above the optics 66. As described above, by means of suitable software installed in the smartphone, e.g. a software app, the smartphone can be used to capture an image result produced within the analysis chamber 71. As has also been discussed above, the smartphone may communicate wirelessly, or via a dock or cable, with a controller of the base unit (e.g. located on the PCB 67) in order to control the test procedure.

Figure 19:
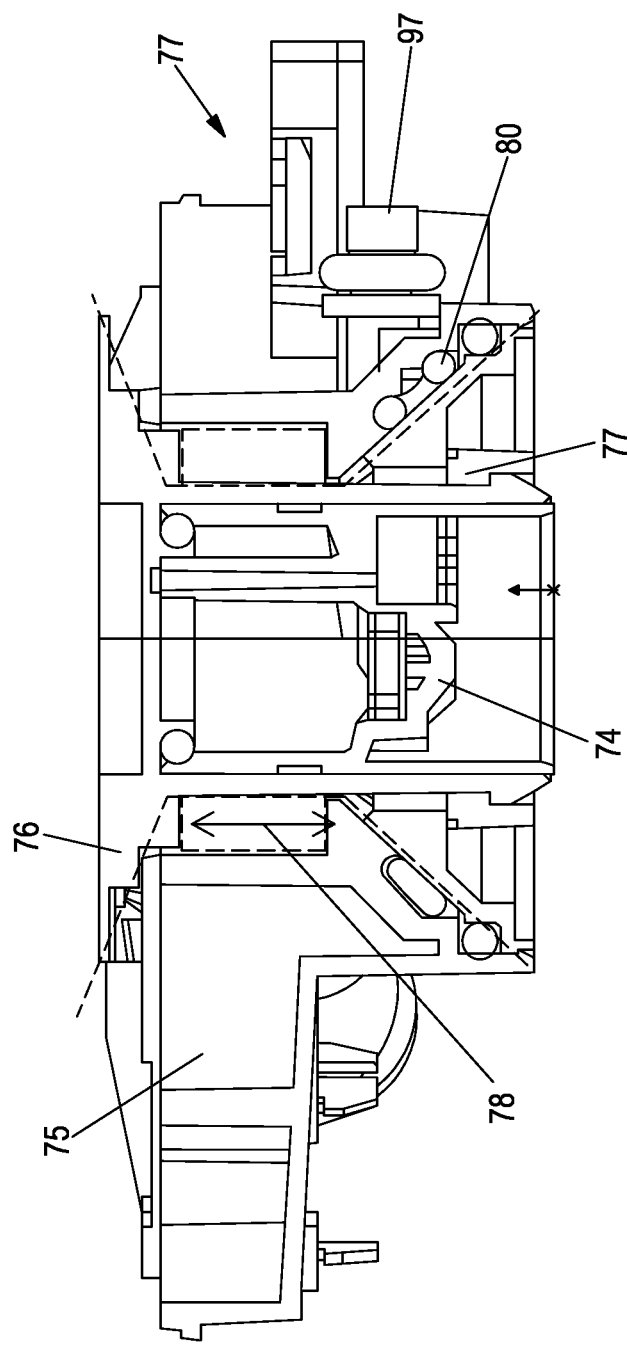
FIG. 19 illustrates a cross-sectional view through a cartridge of the system of FIG. 18.
Figure 20:
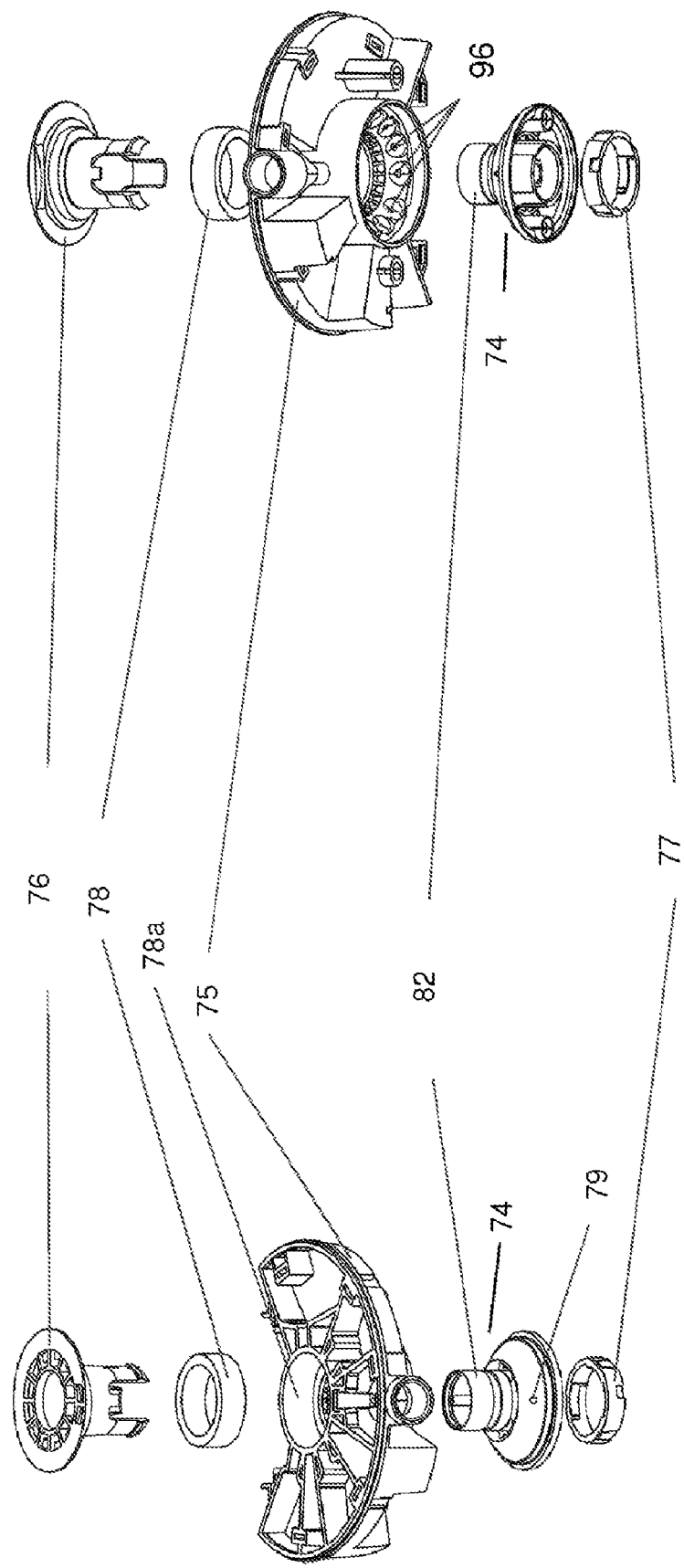
FIG. 20 illustrates exploded component views of the cartridge of FIG. 19 from above (left view) and below (right view)

FIG. 19 shows a cross-section through the test cartridge 70 according to the modified system of FIG. 18. FIG. 20 is an exploded view of the test cartridge from above (left) and below (right). Again, a rotating chamber 74 sits generally within a multi-chamber unit 75. The rotating chamber comprises a cylindrical member 82 defining the flow through chamber. When the test cartridge 70 is docked with the base unit 65, the multi-chamber unit 75 cannot rotate, whilst the rotating chamber 74 is able to rotate under the control of the rotational stepper motor 68. The rotating chamber 74 and multi-chamber unit 75 are secured between an upper wall component 76 and a locking nut 77.

A spring 78 urges the frustoconical surface of the rotating chamber 74 against the opposed inner surface of the multi-chamber unit 75. A main opening 79 (containing a silica frit) is provided in the frustoconical surface of the rotating chamber 48, and communicates with the flow through chamber thereof. A number of apertures 96 are formed around the inner surface of the multi-chamber unit, aligned with respective chambers. Each of these apertures is provided with an elastomeric O-ring 80 which provides sealing against the frustoconical surface of the rotating chamber. The apertures are configured such that the opening 79 in the frustoconical surface can be selectively aligned with apertures in the multi-chamber unit, whilst the O-ring seals prevent leakage from the unaligned apertures of the multi-chamber unit. In the illustrated test cartridge 70, the analysis chamber is not present. Rather, the analysis chamber is plugged into the vacant slot immediately prior to use.

Whilst the construction of the test cartridge 70 differs from that described with reference to FIGS. 2A and 2B, much of the functionality is the same.

As noted briefly above, rather than directly using a piston in the rotating chamber to move fluid between the rotating chamber and the chambers of the multi-chamber unit, this modified system uses a syringe (pump) in the base unit to pneumatically move the liquids. This is illustrated in FIGS.

Figure 21:
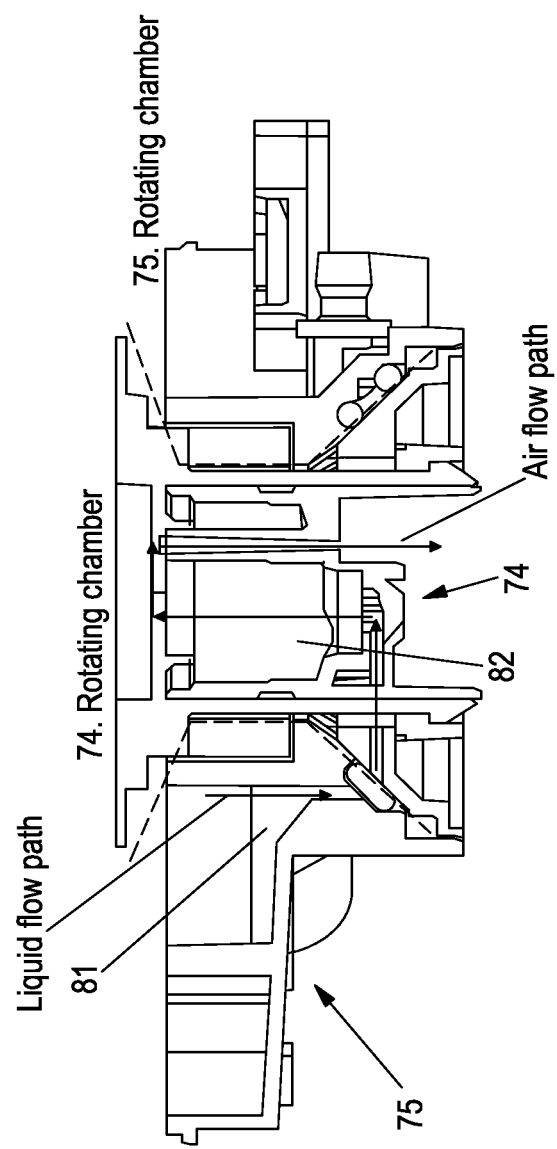
FIG. 21 is a cross-sectional view of the cartridge of FIG. 19 annotated to show liquid and air flow paths through the cartridge in a first operational stage.
Figure 22:
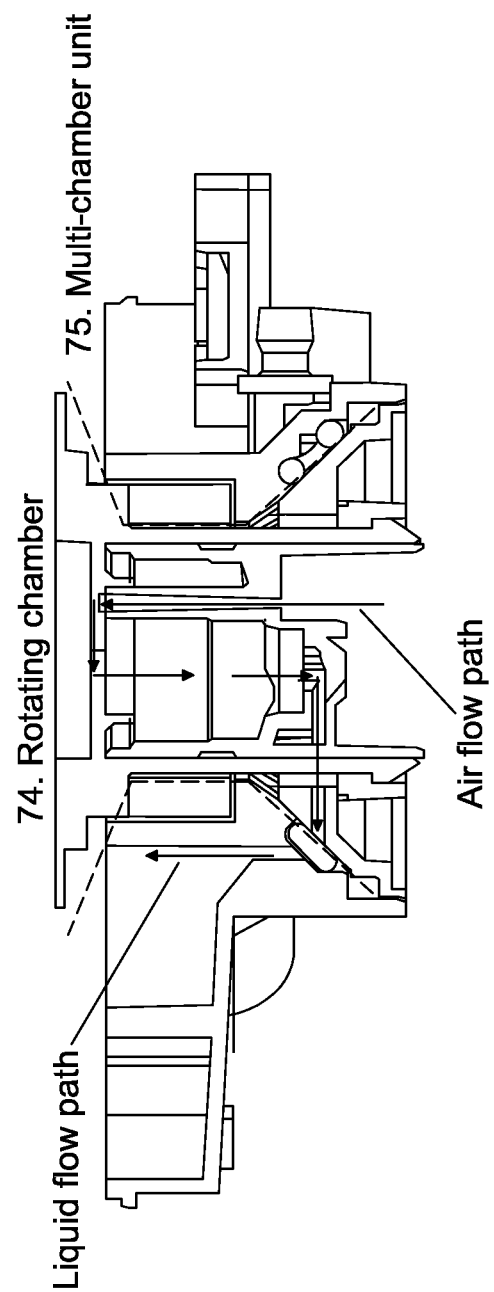
FIG. 22 is a cross-sectional view of the cartridge of FIG. 19 annotated to show liquid and air flow paths through the cartridge in a second operational stage.

21 and 22. FIG. 21 illustrates liquid 81 present within one of the chambers of the multi-chamber unit 75, with the aperture of this chamber being aligned with one of the apertures provided in the rotating chamber 74. Air is drawn by the syringe in the base unit through a path indicated by the series of arrows. This path comprises a rotatable coupling between the base unit and the flow through chamber within the cylindrical member 82. This negative pressure causes liquid to be drawn from the chamber of the multichamber unit, through the aligned apertures, into the flow through chamber within the cylindrical member 82. FIG. 22 illustrates the resulting state, now with a positive pressure being applied to the flow through chamber as indicated by the first set of arrows starting from the right of the Figure. Liquid now begins to flow back from the flow through chamber to the aligned chamber of the multi-chamber unit as indicated by the second set of arrows terminating on the left of the Figure.

Figure 23:
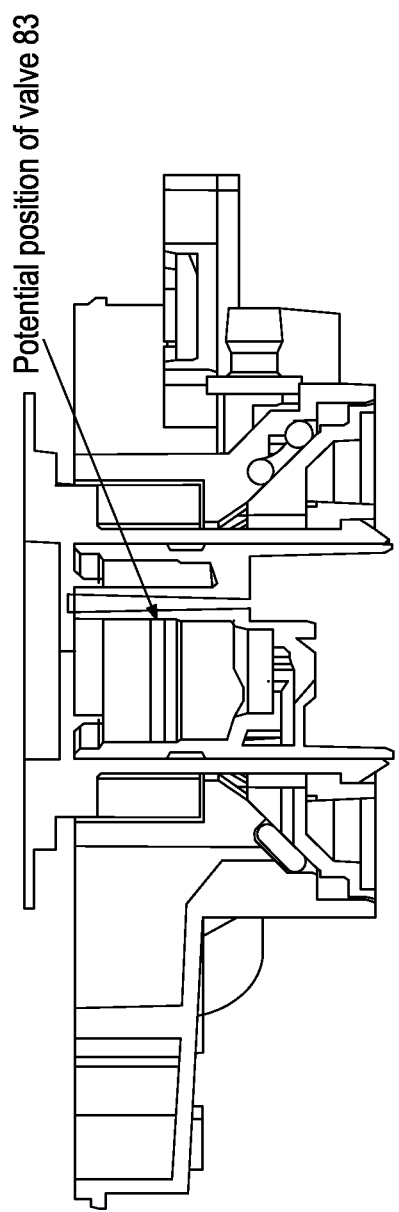
FIG. 23 is a cross-sectional view of the cartridge of FIG. 19 additionally showing a two-way valve within the rotating chamber.

When the rotating chamber 74 is filled with liquid, there may be a risk of liquid splashing upwards and then dropping down into the air flow paths connecting to the base unit. As shown in FIG. 23, the rotating chamber may be provided with a two way valve 83, sitting towards the upper end of the cylindrical member 82. This valve allows air to pass under pressure in both directions, i.e. into and out of the chamber, but prevents splashes from moving to the top of the chamber. The valve may be, for example, a "duck-bill umbrella" valve.

Figure 24:
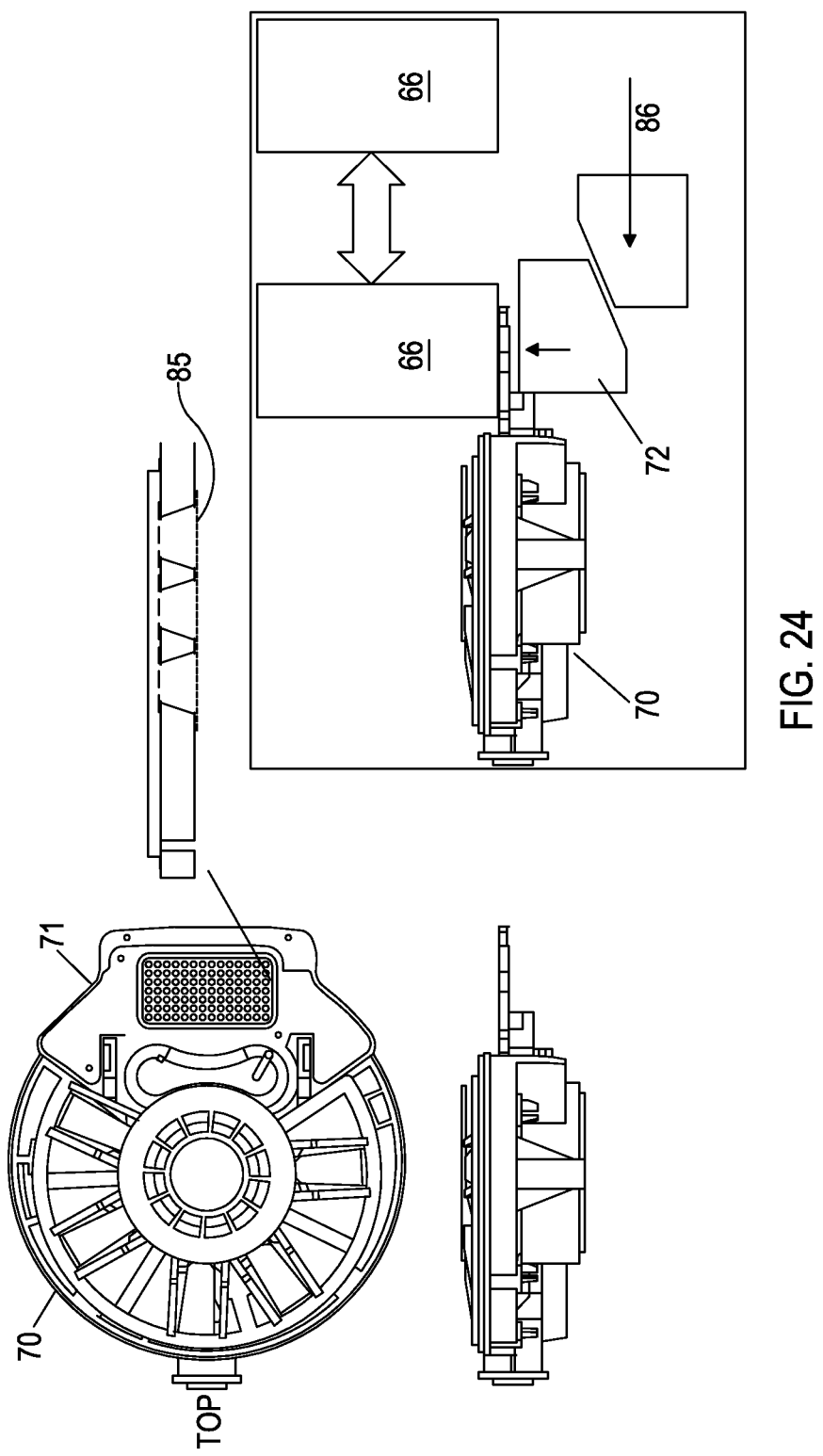
FIG. 24 shows a top plan view of the cartridge of FIG. 19 as well as a side view, a side view annotated to show other components of the system, and a cross-sectional view of a detail of the analysis module including the wells and a fluid inlet into an area above the wells.
Figure 27:
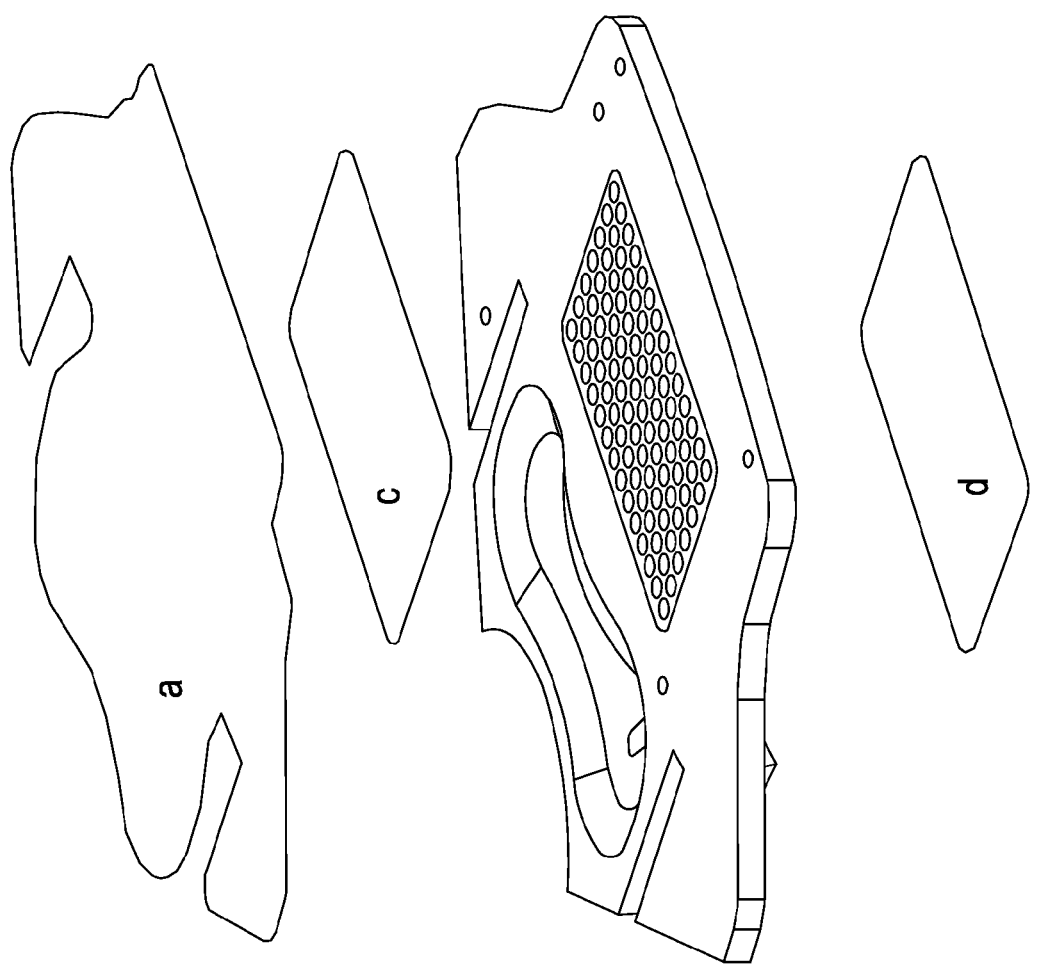
FIG. 27 shows an exploded view of the well array areas of FIGS. 25A and 25B, and FIGS. 26A and 26B.

FIG. 24 illustrates at A a top plan view in cross-section of the test cartridge 70 with the analysis chamber 71 installed. The analysis chamber 71 comprises an array of wells 84 within which the PCR reaction occurs and within which the visible results are produced. In the absence of a sufficiently high liquid injection pressure, it is not generally sufficient to fill the wells by merely flowing liquid across the surface. Rather, a pressure needs to be applied in order to squeeze liquid into the wells. To achieve this, the base 85 of the wells is formed by a material that allows air to pass through but which is impermeable to liquid. Once the test cartridge 70 has been installed into the base unit, the optics 66 slid into place, and liquid transported in the analysis chamber 71 so as to cover the array of wells, a linear actuator 86 is engaged with the Peltier module 72 in order to bias the bottom of the analysis chamber upwards, pressing the top of the analysis chamber against the bottom of the optics. This exerts a pressure on the liquid above the wells, forcing it into the wells in order to achieve satisfactory fill levels. This clamping pressure also ensures good thermal contact between the base of the analysis chamber 71 and the Peltier module 72.

This mechanism for applying pressure above the wells to fill the wells is further illustrated in FIGS. 25A and 25B. As well as a liquid and air impermeable membrane (a) above the wells and a liquid impermeable and air permeable (hydrophobic) layer (d) below the wells, an air and liquid permeable layer (c) is fixed directly on top of the wells beneath the layer (a) and is sealed to the surface between the wells. The purpose of this layer (c) is two-fold. Firstly, it provides resistance to well filling so that the wells do not fill while the volume between layers (a) and (c) is being filled. This minimises the risk of material being carried between wells during filling. Secondly, once the wells are filled the layer (c) can provide some resistance to "cross-talk" between wells. Layer (c) may be relatively hydrophobic with a mesh size sufficient to prevent the passage of liquid unless the liquid pressure exceeds some required level. Cross-talk is also reduced due to the clamping of the layer (a) against the surface by the optics. In some cases layer (c) may be omitted. As will be apparent to the skilled person, one or more biomarkers (e.g. primers/probes) will be provided within the well, or made available to the well, in order to perform the analysis. In one embodiment, the biomarker(s) may be spotted or otherwise fixed to the upper surface the hydrophobic layer (d).

FIGS. 26A and 26B illustrate an alternative mechanism for filling the wells, where filling is from the bottom of the wells. In this case, in addition to the layer (a), a layer (c) which is permeable to air and liquid is provided both above and below the wells, sealed between the wells. In order to allow air to vent from the space above the wells, a small region of the layer (a) is provided as layer (d) being permeable to air but impermeable to liquid. It is also envisaged that a further layer of material that is permeable to air but impermeable to liquid (hydrophobic) may be sandwiched between the lower layer (c) and the base of the wells. In such an arrangement the layer (c) will absorb liquid and bring it into contact with the hydrophobic layer. Under pressure, liquid is then forced through the hydrophobic membrane into the well.

In some cases it may be necessary to provide air flow channels into each of the chambers of the multi-chamber unit in order to allow liquid to flow in and out of the chambers. However, it is preferable that such channels are formed only at the time of use to avoid contamination. FIGS. 28A, 28B and 28C illustrate one possible mechanism for achieving this (a modification to the analysis chamber of FIGS. 19 to 24 and 29A through 29C) and relies upon the provision of a foil or other breakable component on top of each of the chambers. An intermediate component 87 is located above the multi-chamber unit 75 and has a small degree of movement in an axial direction relative to multi-chamber unit. However the component 87 and the multi-chamber unit 75 cannot rotate relative to one another. The upper wall component 76 is modified to include one or more cams 88 which are able to exert a downward force onto the intermediate component 87. When the test cartridge 70 is installed into the base unit 65 and the rotating chamber first rotated together with the upper wall component 76, the cams 88 act to press the component 87 down onto the multi-chamber unit 75. This in turn causes a set of piercing arms 89, aligned with respective chambers, to pierce the foil covers on the chambers thereby venting the chambers to the surrounding environment. Whilst the piercing arms 89 may be raised subsequently as the rotating chamber is further rotated, the venting paths remain open.

FIGS. 29A, 29B and 29C illustrate in more detail the analysis chamber 71. The chamber comprises an array of wells 84 as previously described and a "bone" shaped trough 90 providing a pair of end lobes joined by a central channel. An inlet opening 91 in the base of one of the lobes communicates with the main opening 92 into the analysis chamber. That main opening is the opening that in use is brought into communication with the opening 79 of the rotating chamber via a channel of the multichamber unit. When the analysis chamber 71 is plugged into the multi-chamber unit the opening 92 communicates with this channel. The channel is identified in FIG. 19 by reference numeral 97. An outlet opening 93 in the other of the lobes communicates with an well injection opening 94 adjacent to the wells. The Figure shows a lyophilized (or freeze dried) particle 95 present in the inlet opening 91. This particle 95 comprises so-called "mastermix" that is dissolved into liquid as liquid flows from the main chamber opening 92 to the trough 90. [NB. In other embodiments mastermix may be provided as a dried component elsewhere in the analysis chamber or could be provided in liquid form in another chamber of the multichamber unit 75.]

Figure 30:
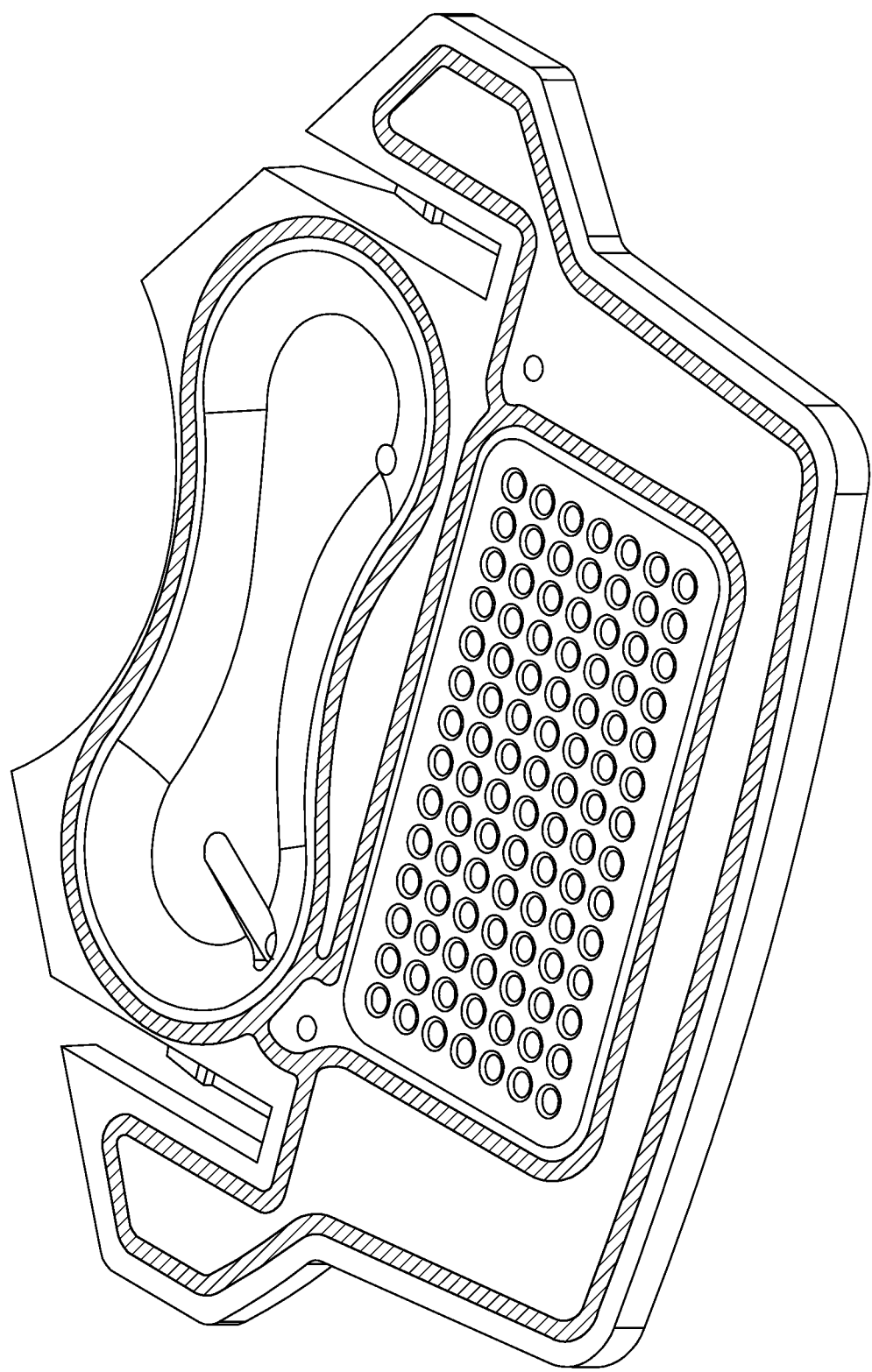
FIG. 30 is a top perspective view of a base of the cartridge and identifying welding locations for an upper sheet.

Although not shown in FIGS. 29A, 29B and 29C, the analysis chamber 71 is covered by a transparent, plastic sheet that is welded around the periphery of the chamber 71. The plastic sheet is further welded to the top of the chamber 71 to provide pockets above the trough 90 and the array of wells 84 that are isolated from one another. [Welding locations are shown in red in FIG. 30.] This ensures that liquid can only pass from one pocket to the other via the openings 91, 93. It is further noted that the base of the trough 90 is slightly inclined, such that when the top of the chamber 71 is level, as is the case in use, the base of the outlet lobe of the trough 90 is lower than the base of the inlet end of the trough. A centrally located waist of the trough 90 also provides a restriction to the flow of liquid from the inlet side to the outlet side, and is further raised slightly with respect to the bottom of both sides. This arrangement helps to avoid the formation of bubbles in the liquid as the trough is filled and improves mixing. It will be appreciated that, in use, as the Peltier module 72 is pushed upwards (FIG. 24), the plastic membrane on top of the chamber 71 is pressed against the bottom of the optics 66, forcing the membrane against the surface of the chamber and creating a pressure to cause filling of the wells.

With reference again to the partial cross-sectional view of the array of wells shown in FIG. 24 (inset), in vertical cross-section the wells are defined by inclined walls so that the area of the base of the wells is greater that the area of the top of the wells. Whilst this structure facilitates injection moulding of the chamber, it has also been found to be advantageous in reducing or avoiding the accumulation of materials on the sidewalls.

Figure 31:
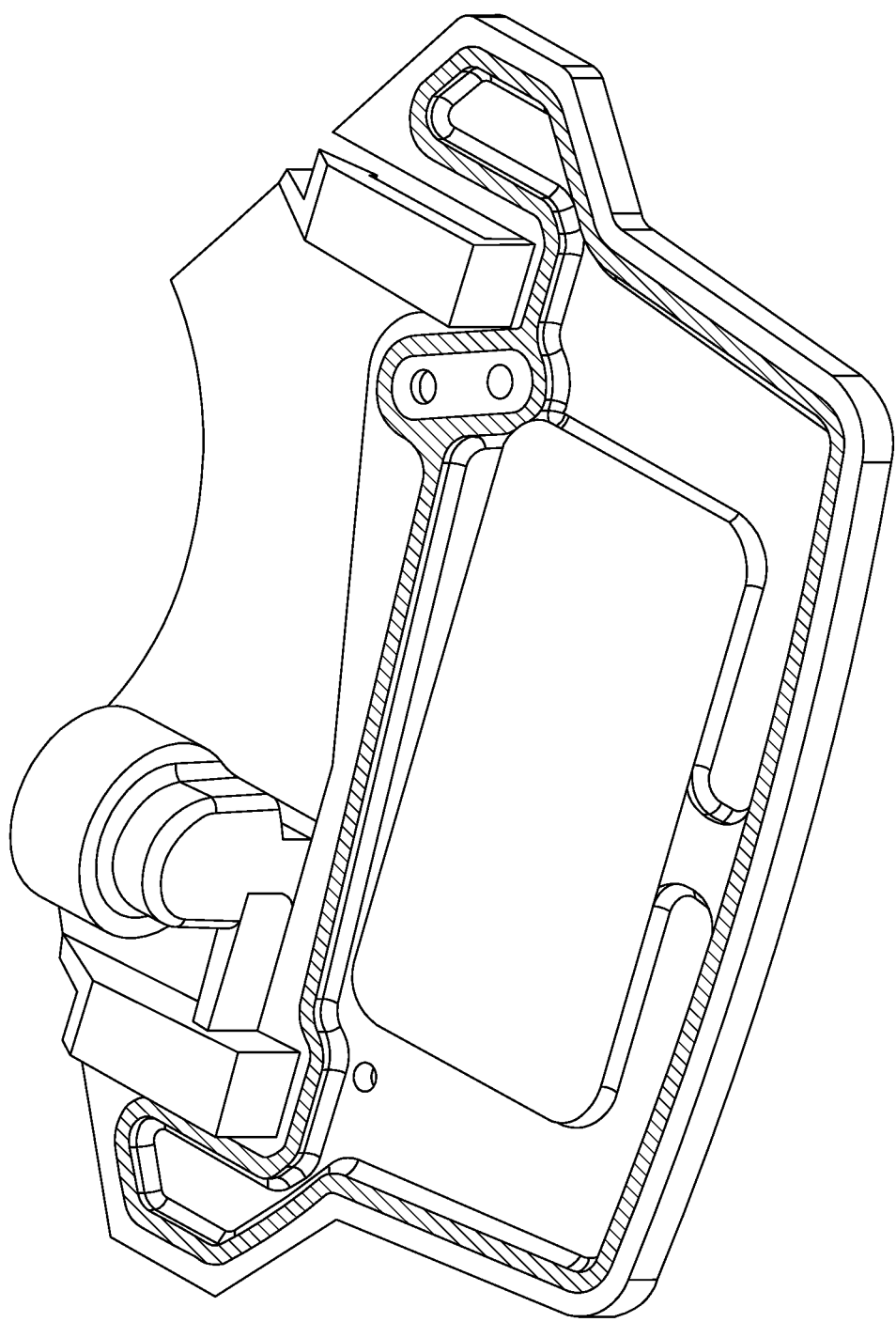
FIG. 31 is a bottom perspective view of a base of the cartridge and identifying welding locations for a lower hydrophobic membrane.

FIG. 31 shows, in hashed lines, where a further, air and liquid impermeable membrane may be welded to the base of the cartridge. It is also noted that a pair of voids are provided on either side of the bottom of the well array, i.e. under the further sheet. As already described, the base of the wells are covered with a first air-permeable (hydrophobic) membrane while the entire well plus void areas are covered by the further membrane which is elastomeric. During filling of the wells, air from the wells exits through the first hydrophobic membrane and fills the space enclosed by the second, further membrane. This air acts as an insulating medium allowing more even heat distribution across the well array during thermal cycling.

It is required to isolate the air from the contents of the wells during thermal cycling, to prevent evaporation. The clamping of the analysis chamber between the Peltier and the optics acts as a valve to shut off the air path between the base of the wells and the air voids. The position of the weld line in FIG. 31 is important as it allows a good seal between the Peltier unit and the base of the wells (if there was a weld in that region, the seal would be poor).

In operation, and to further clarify the description above, the optics module seals across the upper surface of the well area, preventing liquid communication between the wells. The Peltier module seals across the base of the wells, preventing air communication between the wells and voids. In both cases we want to avoid valving in a region with a weld line.

It will be appreciated by the person of skill in the art that various modifications may be made to the above described embodiments without departing from the scope of the invention. For example, it may be advantageous to form the base of the analysis chamber 71 as two distinct components, namely a first component in which the wells are formed and which is made of a material with a relatively high thermal conductive, and a second component surrounding the first component and that is made of a material having a relatively low thermal conductivity. This arrangement may assist with the rapid heating and cooling cycles performed during an analysis. Alternatively, or in addition, isolation tracks may be provided around the array of wells to provide a degree of thermal isolation to the array. In another modification to the analysis chamber, each well may be surrounded at its upper opening by an upwardly projecting lip or rim. The rims will provide the regions of contact against the liquid and air impermeable membrane (a) when that membrane is pressed down as it is pressed against the optics. This increases the sealing pressure around each well.

| Reference numeral | Component description |
| --- | --- |
| 1 | SNP genotyping system |
| 2 | Base unit |
| 3 | Test cartridge |
| 4 | Button |
| 5 | Upper multi-chamber unit |
| 5a-f | chambers |
| 6 | Lower unit |
| 7 | rotating chamber |
| 8 | radially extending walls |
| 9 | interior space |
| 10 | closed upper surface |
| 11 | cylindrical wall |
| 12 | Radially extending holes |
| 13 | circular opening |
| 14 | Cylindrical member |
| 15 | Upper wall |
| 16 | Circular opening |
| 17 | Cylindrical wall |
| 18 | inwardly protruding lip |
| 19 | bevelled gear wheel |
| 20 | plunger head |
| 21 | capture feature |
| 22 | Component (chip module) |
| 23 | open segment of upper unit |
| 24 | outer housing |
| 25 | first rotary motor |
| 26 | bevelled pinion |
| 27 | controller |
| 28 | second rotary motor |
| 29 | first gear wheel |
| 30 | second gear wheel |
| 31 | lead screw |
| 32 | capture head |
| 33 | Radially extending opening |
| 34 | Buccal swab |
| 35 | Buccal swab collection end |
| 36 | Buccal swab handle |
| 37 | Access port |
| 50 | Base unit (second embodiment) |
| 51 | Docking station |
| 52 | Smartphone |
| 53 | Test cartridge |
| 54 | cartridge reception port |
| 55 | smartphone |
| 56 | instrument |
| 57 | Docking compartment |
| 58 | camera |
| 59 | controller |
| 60 | Instrument memory |
| 61 | Smartphone memory |
| 62 | Product database |
| 63 | Smartphone processor |
| 64 | Silica frit |
| 65 | Base unit |
| 66 | Optics |
| 67 | PCB |
| 68 | Rotational stepper motor |
| 69 | Syringe |
| 70 | Test cartridge |

-continued

| Reference numeral | Component description |
|---|---|
| 71 | Analysis chamber |
| 72 | Peltier module |
| 73 | Smartphone |
| 74 | Rotating chamber |
| 75 | Multi-chamber unit |
| 76 | Upper wall component |
| 77 | Locking nut |
| 78 | Spring |
| 78a | Spring pocket |
| 79 | Opening to flow through chamber |
| 80 | O-ring |
| 81 | Liquid |
| 82 | Cylindrical member |
| 83 | Two-way valve |
| 84 | Array of wells |
| 85 | Well base |
| 86 | Linear actuator |
| 87 | Intermediate component |
| 88 | Cams |
| 89 | Piercing arms |
| 90 | Trough |
| 91 | Inlet opening |
| 92 | Main opening |
| 93 | Outlet opening |
| 94 | Well injection opening |
| 95 | Lyophilized particle |
| 96 | Apertures in the multichamber unit |
| 97 | Channel provided in multichamber unit |

The invention claimed is:

1. A system for preparing and analysing a sample of biological material, the system comprising:
   a test cartridge having
      a first housing defining a flow-through chamber,
      a second housing defining a central space within which the first housing is at least partially located, the first housing being rotatable relative to the second housing about an axis but without permitting any relative movement along said axis between the housings, and the second housing defining a plurality of circumferentially spaced chambers, one of the plurality of circumferentially spaced chambers having an inlet for receiving a sample, at least one of the plurality of circumferentially spaced chambers containing a liquid reagent, and at least one of the plurality of circumferentially spaced chambers comprising an analysis module, the plurality of circumferentially spaced chambers of the second housing each having an opening into said central space at the same axial position,
   wherein the first housing has one or more openings into said central space at said axial position so that the or each opening can be selectively aligned with one of the openings into the plurality of circumferentially spaced chambers of the second housing by relative rotation of the first housing and second housings,
   a base unit having
      a dock housing defining or having connected thereto features for docking the test cartridge with the base unit so that the second housing cannot rotate with respect to the base unit whilst the first housing can rotate relative to the base unit,
      a first driver for engaging with said first housing to cause rotation of the first housing within the second housing,
      a second driver for positively and negatively pressurising the flow-through chamber of the first housing,
      a controller for operating the first and second drivers to cause displacement of liquids between the plurality of circumferentially spaced chambers in a desired sequence, resulting in the delivery of a prepared sample to one of the plurality of circumferentially spaced chambers containing an analysis module, thereby facilitating provision of an analysis result by the analysis module,
   an optical component moveable to a position above the dock housing,
   wherein said one of said chambers that contains the analysis module has a transparent window in its upper surface, and said analysis module comprises an array of wells across a planar surface that is substantially orthogonal to said axis and is configured to provide a visually detectable analysis result in said wells that is visible from above the system through said transparent window and through said optical component when a cartridge is docked in said dock housing.

2. A system according to claim 1, wherein said chambers of the second housing are defined in part by a generally cylindrical wall which also defines said central space, the openings of the chambers being provided as openings through the cylindrical wall.

3. A system according to claim 1 and further comprising a piston movable axially within the flow through chamber of the first housing, and said second driver cooperating with said piston to positively and negatively pressurise the flow-through chamber.

4. A system according to claim 1 and comprising air flow channels defined in the base unit and the test cartridge, said second driver comprising a piston and cylinder in fluid communication with the air flow channels when the test cartridge is docked with the base unit.

5. A system according to claim 1, wherein the second housing further defines at least one empty chamber for venting or receiving waste liquid.

6. A system according to claim 5, said test cartridge comprising a third housing fixed beneath the second housing and being in liquid communication with the or each said empty chamber.

7. A system according to claim 1, wherein features for docking the test cartridge with the base unit are configured to prevent rotation of the second housing with respect to the base unit, a base of the first housing having gear teeth arranged around a circumferential region, said first driver comprising a rotary motor for driving a pinion that is engaged with said gear teeth of the first housing so that rotation of the pinion by the rotary motor causes the first housing to rotate within the second housing.

8. A system according to claim 7, wherein said gear teeth and said pinion have complimentary bevels so that the pinion sits over the gear teeth.

9. A system according to claim 8, said pinion having a cut-away section which, when aligned with the gear teeth of the first housing, allow docking and removal of the test cartridge with and from the base unit.

10. A system according to claim 1, wherein said inlet for receiving a sample is configured to receive a sample head of a swab.

11. A system according to claim 1, the system being configured to perform Single Nucleotide Polymorphism genotyping, and the chambers of the test cartridge comprising at least a chamber containing a lysis buffer, a chamber containing a wash liquid reagent, and a chamber containing an elution reagent.

12. A system according to claim 11, said analysis module being configured to perform DNA amplification and having an interface to indicate amplification.

13. A system according to claim 1 and comprising features for facilitating docking of a smartphone with the system so that an analysis result of the analysis module can be imaged by a camera of the smartphone.

14. A system according to claim 1, said first housing comprising a porous membrane within or in liquid communication with said flow through chamber, the porous membrane being configured to retain DNA material.

15. A system according to claim 14 wherein said porous membrane is a silica frit.

16. A system according to claim 14, wherein said first housing comprises two or more of said openings into the central space, at least one of the openings being unimpeded and another of the openings being impeded by said porous membrane.

17. A system according to claim 16 and being configured such that when one of the impeded and unimpeded openings is aligned with one of the openings into the chambers of the second housing, the other of the impeded and unimpeded openings is not so aligned.

18. A system according to claim 1, wherein said analysis module is a plug-in module.

19. A system according to claim 1, wherein said base unit comprises components configured to apply pressure between upper and lower surfaces of said analysis module in order to control liquid flow within the analysis module.

20. A system according to claim 19, wherein one of said components is a Peltier module.

* * * * *